US011957812B2

(12) United States Patent
Suh et al.

(10) Patent No.: US 11,957,812 B2
(45) Date of Patent: Apr. 16, 2024

(54) SILICON NITRIDE IMPLANTS AND COATINGS

(71) Applicant: CTL Medical Corporation, Addison, TX (US)

(72) Inventors: Sean Suh, Milltown, NJ (US); Jon Suh, Ambler, PA (US)

(73) Assignee: CTL Medical Corporation, Addison, TX (US)

(*) Notice: Subject to any disclaimer, the term of this patent is extended or adjusted under 35 U.S.C. 154(b) by 594 days.

(21) Appl. No.: 16/726,043

(22) Filed: Dec. 23, 2019

(65) Prior Publication Data

US 2020/0197565 A1 Jun. 25, 2020

Related U.S. Application Data

(60) Provisional application No. 62/812,833, filed on Mar. 1, 2019, provisional application No. 62/809,400, filed on Feb. 22, 2019, provisional application No. 62/795,418, filed on Jan. 22, 2019, provisional application No. 62/783,447, filed on Dec. 21, 2018, provisional application No. 62/783,491, filed on Dec. 21, 2018.

(51) Int. Cl.
*A61F 2/44* (2006.01)
*A61F 2/30* (2006.01)
*A61L 27/28* (2006.01)

(52) U.S. Cl.
CPC ............ *A61L 27/28* (2013.01); *A61F 2/3094* (2013.01); *A61F 2/4455* (2013.01); *A61F 2002/30003* (2013.01); *A61F 2240/001* (2013.01); *A61F 2310/00874* (2013.01)

(58) Field of Classification Search
CPC ...... A61F 2/4455; A61F 2/446; A61F 2/4465; A61F 2/447
See application file for complete search history.

(56) References Cited

U.S. PATENT DOCUMENTS 10,034,768 B2 * 7/2018 Gray ................. A61B 17/8042
2011/0052660 A1 * 3/2011 Yang ..................... C04B 35/447
424/426

OTHER PUBLICATIONS

Arts et al., Porous silicon nitride spacers versus PEEK cages for anterior cervical discectomy and fusion: clinical and radiological results of a single-blinded randomized controlled trial, Oct. 19, 2016, European SPine Journal (2017), pp. 2372-2380. (Year: 2017).*

* cited by examiner

*Primary Examiner* — Brian A Dukert
(74) *Attorney, Agent, or Firm* — BRAINSPARK ASSOCIATES. LLC

(57) ABSTRACT

Disclosed are devices, systems and/or methods for use in the surgical treatment of vertebrae and/or other bones, particularly implants and/or related devices comprising silicon nitride in some of all of the implant or device body, including portions, layers and/or surface coatings thereof, for use in spinal surgeries and/or other orthopedic procedures.

16 Claims, 24 Drawing Sheets

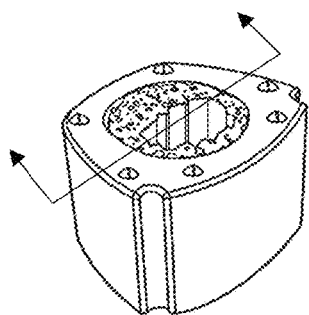
FIG. 10
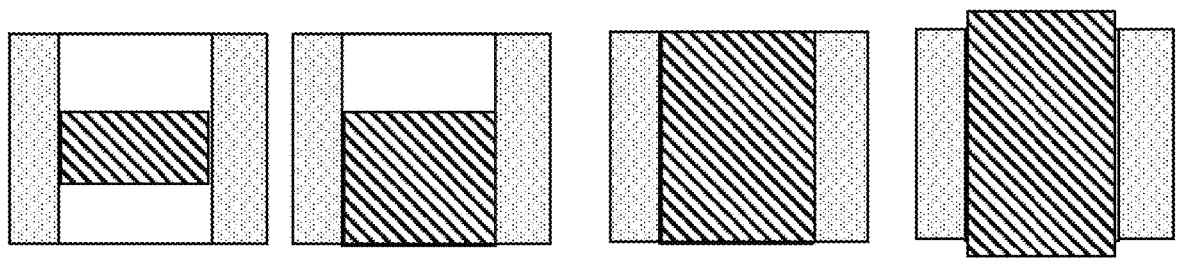
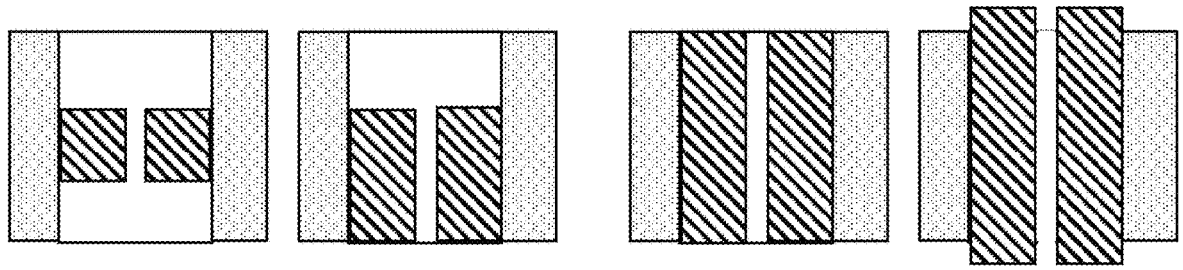
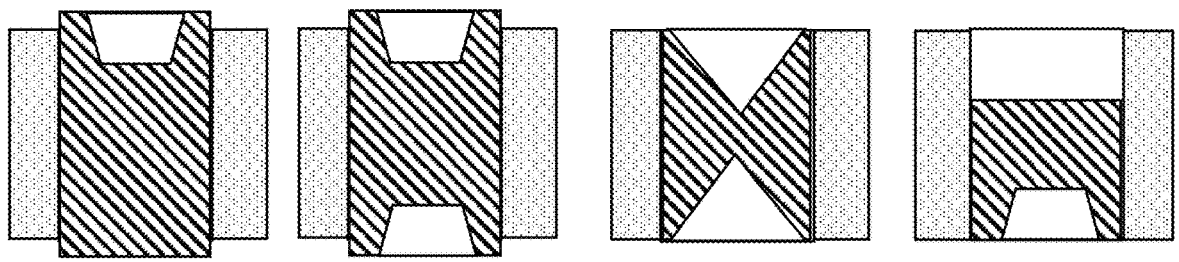
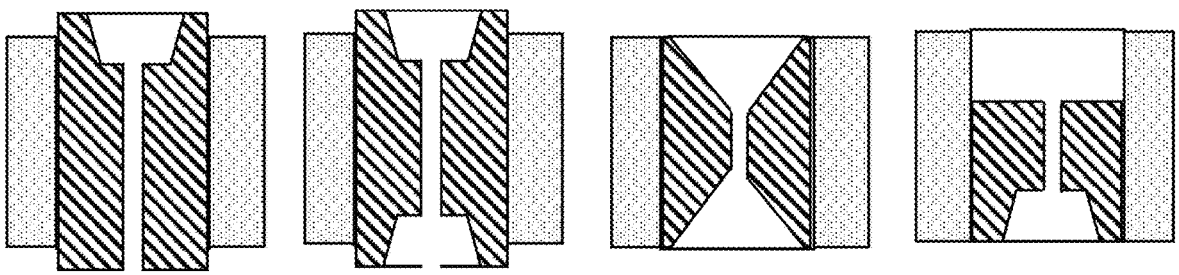

Polyetheretherketone

Medical grade Ti Metal

"As-Fired" $Si_3N_4$

SiYAlON-Glazed $Si_3N_4$ $N_2$-Treated $Si_3N_4$

Oxidized $Si_3N_4$

Bone Ingrowth 5.5mm

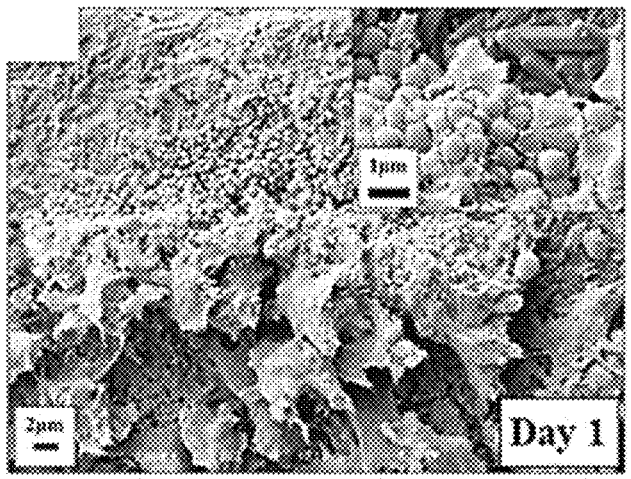
FIG. 14A
FIG. 14B
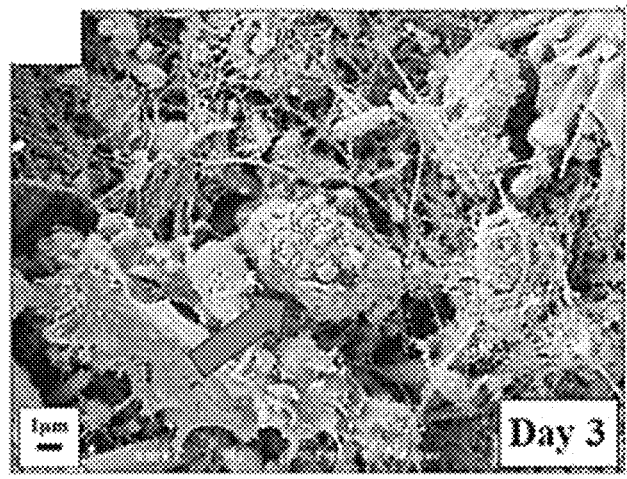
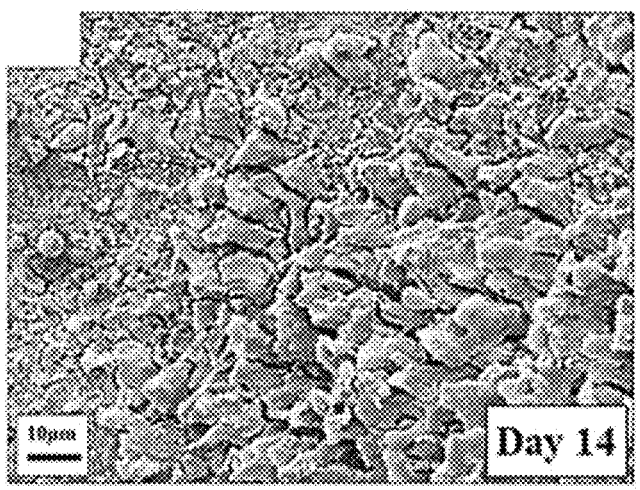
FIG. 14C 1300
1310

SILICON NITRIDE IMPLANTS AND COATINGS

CROSS-REFERENCE TO RELATED APPLICATIONS

This application claims priority to and benefit of U.S. Provisional Patent Application No. 62/783,447 entitled "Bone Growth Enhancing Screws" filed Dec. 21, 2018; U.S. Provisional Patent Application No. 62/783,491 entitled "ANTI-ROTATION RODS" filed Dec. 21, 2018; U.S. Provisional Patent Application No. 62/795,418 entitled "BONE GRAFT BLOCK GEOMETRY" filed Jan. 22, 2019; U.S. Provisional Patent Application No. 62/809,400 entitled "POROUS CAGE WITH IMPACTION INSERT" filed Feb. 22, 2019 and U.S. Provisional Patent Application No. 62/812,833 entitled "BONE GROWTH ACTIVATION IMPLANTS" filed Mar. 1, 2019. The disclosures of each of these references are incorporated by reference herein in their entireties.

FIELD OF THE INVENTION

The present subject matter relates generally to implants and related devices comprising silicon nitride in some of all of the implant body, including portions, layers and/or surface coatings thereof, including orthopedic implants such as joint and/or bone replacement implants used in in spinal surgeries, dental surgeries and/or other orthopedic procedures.

BACKGROUND OF THE INVENTION

The spinal column of vertebrates provides support to bear weight and protection to the delicate spinal cord and spinal nerves. The spinal column includes a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Between each vertebral body is an intervertebral disk, a cartilaginous cushion to help absorb impact and dampen compressive forces on the spine. To the posterior, the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition, congenital or acquired deformities can cause abnormal angulation or slippage of the spine. Anterior slippage (spondylolisthesis) of one vertebral body on another can cause compression of the spinal cord or nerves. Patients who suffer from one of more of these conditions often experience extreme and debilitating pain and can sustain permanent neurological damage if the conditions are not treated appropriately.

Various physical conditions can manifest themselves in the form of damage or degeneration of an intervertebral disc, the result of which is mild to severe chronic back pain. Intervertebral discs serve as "shock" absorbers for the spinal column, absorbing pressure delivered to the spinal column. Additionally, they maintain the proper anatomical separation between two adjacent vertebrae. This separation is necessary for allowing both the afferent and efferent nerves to exit and enter, respectively, the spinal column. Alternatively, or in addition, there are several types of spinal curvature disorders. Examples of such spinal curvature disorders include, but need not be limited to, lordosis, kyphosis and scoliosis.

One technique of treating spinal disorders, in particular the degenerative, traumatic and/or congenital issues, is via surgical arthrodesis of the spine. This can be accomplished by removing the intervertebral disk and replacing it with implant(s) and/or bone and/or immobilizing the spine to allow the eventual fusion or growth of the bone across the disk space to connect the adjoining vertebral bodies together. The stabilization of the vertebra to allow fusion is often assisted by the surgically implanted device(s) to hold the vertebral bodies in proper alignment and allow the bone to heal, much like placing a cast on a fractured bone. Such techniques have been effectively used to treat the above-described conditions and in most cases are effective at reducing the patient's pain and preventing neurological loss of function.

Complications of joint fusions and/or other procedures of the spine can include those applicable to any surgery such as bone and/or soft-tissue infection, wound dehiscence, and failure of fixation. Other complications which may be more specific to fusion procedures can include malalignment, proximal or distal joint deterioration, and delayed union or nonunion, including potential complications resulting from medical comorbidities, patient noncompliance, and/or inappropriate fixation. Accordingly, there is need for further improvement in surgical implants, and the present subject matter is such improvement.

BRIEF SUMMARY OF THE INVENTION

The following presents a simplified summary of the subject matter in order to provide a basic understanding of some aspects of the subject matter. This summary is not an extensive overview of the subject matter. It is intended to neither identify key or critical elements of the subject matter nor delineate the scope of the subject matter. Its sole purpose is to present some concepts of the subject matter in a simplified form as a prelude to the more detailed description that is presented later.

In accordance with various aspects of the present subject matter, implant devices and/or components thereof are described that incorporate silicon nitride (i.e., $Si_3N_4$ and/or chemical analogues thereof) in their construction, either in the entirety of the implant as well as components, portions, layers and/or surfaces thereof. In various embodiments, the silicon nitride material(s) will be highly osteo-inductive and/or osteoconductive and will desirably facilitate and/or promote implant fixation to adjacent living bone surfaces, while concurrently reducing and/or inhibiting periprosthetic infection and/or bacterial adhesion to the surfaces and/or interior portions of the implant.

In various applications, the utility of silicon nitride as an implant material can be enhanced by the addition of various other medical materials, including the use of one or various combinations of titanium, chrome cobalt, stainless steel, silicone, poly (ether ether ketone) (PEEK), ultra-high molecular-weight polyethylene (UHMWPE), polyurethane foams, polylactic acid, apatites and/or various 3D printed materials. In such cases, the employment of such material mixtures in implant construction may enhance the strength and/or durability of a desired implant design, as well as allow for improved surgical outcomes and/or greatly reduced complication rates.

If desired, implants can be constructed from a variety of modular components, including modular components comprising different materials. If desired, such modular components could be provided in a kit form for selection and/or assembly in a surgical theatre and/or in situ during a surgical procedure. If desired, various components may be removable and replaceable.

Various surgical methods for preparing anatomical surfaces and/or for implanting or placement of the various devices and/or components described herein are also described, including the insertion and placement of implants between adjacent vertebrae of the spine as well as within bones and/or between other joint surfaces.

In accordance with another aspect of the present subject matter, various methods for manufacturing devices and/or components thereof, as set for within any of the details described with the present application, are provided.

While embodiments and applications of the present subject matter have been shown and described, it would be apparent that other embodiments, applications and aspects are possible and are thus contemplated and are within the scope of this application.

The following description and the annexed drawings set forth in detail certain illustrative aspects of the subject matter. These aspects are indicative, however, of but a few of the various ways in which the principles of the subject matter may be employed and the present subject matter is intended to include all such aspects and their equivalents. Other objects, advantages and novel features of the subject matter will become apparent from the following detailed description of the subject matter when considered in conjunction with the drawings.

BRIEF DESCRIPTION OF THE SEVERAL VIEWS OF THE DRAWINGS

The foregoing and other features and advantages of the present subject matter will become apparent to those skilled in the art to which the present subject matter relates upon reading the following description with reference to the accompanying drawings. It is to be appreciated that two copies of the drawings are provided; one copy with notations therein for reference to the text and a second, clean copy that possibly provides better clarity.

FIG. 10 depicts various cross-sectional views of a spinal implant with various exemplary silicon nitride insert geometries formed therein;

FIGS. 14A through 14C depict exemplary effects of a silicon nitride surface on bacteria near the implant;

DETAILED DESCRIPTION OF THE INVENTION

Figure 1:
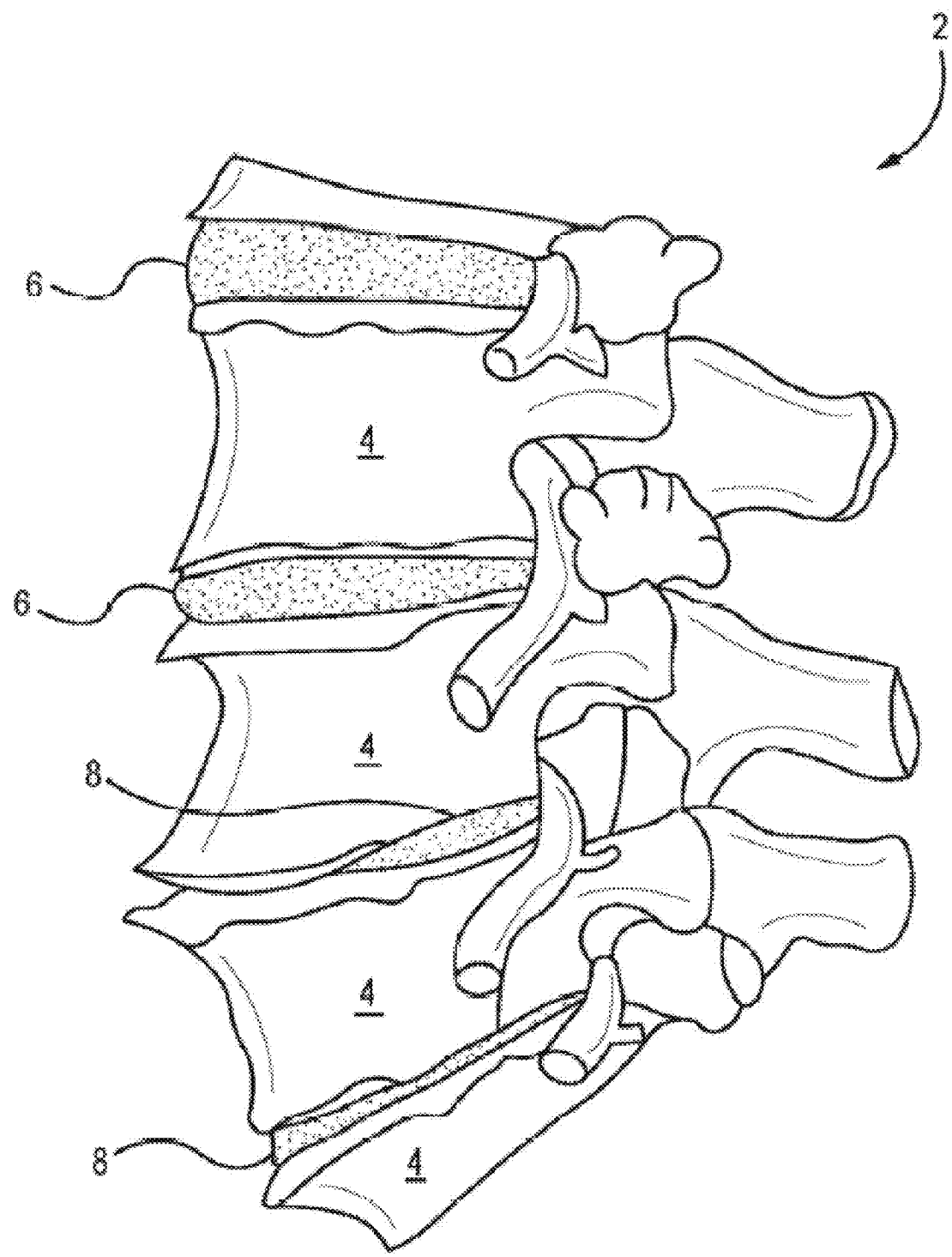
FIG. 1 illustrates a portion of a patient's spinal column.

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

The terms "including," "comprising" and variations thereof, as used in this disclosure, mean "including, but not limited to," unless expressly specified otherwise. The terms "a," "an," and "the," as used in this disclosure, mean "one or more," unless expressly specified otherwise.

Devices and/or device components that are disclosed in communication with each other need not necessarily be in continuous communication with each other, unless expressly specified otherwise. In addition, devices that are in direct contact with each other may contact each other directly or indirectly through one or more intermediary articles or devices. The device(s) disclosed herein may be made of a material such as silicon nitride, which may alternatively be combined, in various embodiments, with other materials such as, for example, a polymer, a metal, an alloy, or the like. For instance, the device(s) may comprise silicon nitride, alone or in combination with a Polyether Ether Ketone (PEEK), titanium, a titanium alloy, or the like, or various combinations of the foregoing. The material may be formed by a process such as, for example, an active reductive process of a metal (e.g., titanium or titanium alloy) to increase the amount of nanoscaled texture to device surface(s), so as to increase promotion of bone growth and fusion.

Although process steps, method steps, or the like, may be described in a sequential order, such processes and methods may be configured in alternate orders. In other words, any sequence or order of steps that may be described does not necessarily indicate a requirement that the steps be performed in that order. The steps of the processes or methods described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device or article may be alternatively embodied by one or more other devices or articles which are not explicitly described as having such functionality or features.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides various devices, systems and methods for treating various anatomical structures of the spine and/or other areas of human and/or animal bodies. While the disclosed embodiments may be particularly well suited for use during surgical procedures for the repair, fixation and/or support of vertebrae, it should be understood that various other anatomical locations of the body may benefit from various features of the present invention.

The spinal column of vertebrates provides support to bear weight and protection to the delicate spinal cord and spinal nerves. The spinal column includes a series of vertebrae stacked on top of each other. There are typically seven cervical (neck), twelve thoracic (chest), and five lumbar (low back) segments. Each vertebra has a cylindrical shaped vertebral body in the anterior portion of the spine with an arch of bone to the posterior, which covers the neural structures. Between each vertebral body is an intervertebral disk, a cartilaginous cushion to help absorb impact and dampen compressive forces on the spine. To the posterior, the laminar arch covers the neural structures of the spinal cord and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition, congenital or acquired deformities can cause abnormal angulation or slippage of the spine. Anterior slippage (spondylolisthesis) of one vertebral body on another can cause compression of the spinal cord or nerves. Patients who suffer from one of more of these conditions often experience extreme and debilitating pain, and can sustain permanent neurological damage if the conditions are not treated appropriately. Alternatively or in addition, there are several types of spinal curvature disorders. Examples of such spinal curvature disorders include, but need not be limited to, lordosis, kyphosis and scoliosis.

One technique of treating spinal disorders, in particular the degenerative, traumatic and/or congenital issues, is via surgical arthrodesis of the spine. This can be accomplished by removing the intervertebral disk and replacing it with implant(s) and/or bone and immobilizing the spine to allow the eventual fusion or growth of the bone across the disk space to connect the adjoining vertebral bodies together. The stabilization of the vertebra to allow fusion is often assisted by the surgically implanted device(s) to hold the vertebral bodies in proper alignment and allow the bone to heal, much like placing a cast on a fractured bone. However, while such techniques have been effectively used to treat the above-described conditions and can be effective at reducing the patient's pain and preventing neurological loss of function, current bone implants (1) typically play a passive role as a bone replacement structure and do not contribute significantly to bone growth, (2) often create interference, distortion and/or imaging artifacts during non-invasive imaging of a treated anatomical region, (3) often require a blood pathway between bridging elements, such as by requiring the end user to ensure that proper amounts of blood conducting agents have been added and/or packed along and/or around the implant, (4) often have porous openings, tessellated supports and/or other structural features that are difficult to fabricate and that require specialized or expensive fabrication methods, (5) are often made of materials such as metals or polymers that do not induce bone growth or only allow a thin film of bone to adhere to the implant materials, and (6) do not provide anti-bacterial properties. Because of this, such procedures are still associated with significant levels of surgical complications such as non-unions and/or infections, and thus there is need for further improvement. The present subject matter is such improvement.

The present subject matter will now be described with reference to the drawings, wherein like reference numerals are used to refer to like elements throughout. It is to be appreciated that the various drawings are not necessarily drawn to scale from one figure to another nor inside a given figure, and in particular that the size of the components may be arbitrarily drawn for facilitating the understanding of the drawings. In the following description, for purposes of explanation, numerous specific details are set forth in order to provide a thorough understanding of the present subject matter. It may be evident, however, that the present subject matter can be practiced without these specific details. Additionally, other embodiments of the subject matter are possible and the subject matter is capable of being practiced and carried out in ways other than as described. The terminology and phraseology used in describing the subject matter is employed for the purpose of promoting an understanding of the subject matter and should not be taken as limiting.

In various embodiments, the implants and/or portions may comprise silicon nitride and/or various combinations of a variety of surgically acceptable materials, including radiopaque and/or radiolucent materials, other materials or combinations of such materials. Radiolucent materials can include, but are not limited to, polymers, carbon composites, fiber-reinforced polymers, plastics, combinations thereof and the like. Radiopaque materials are traditionally used to construct devices for use in the medical device industry. Radiopaque materials can include, but are not limited to, metal, aluminum, stainless steel, titanium, titanium alloys, cobalt chrome alloys, combinations thereof and the like.

FIG. 1 depicts a portion of a patient's spinal column 2, including vertebrae 4 and intervertebral discs 6. In humans, the spinal column is generally formed by individual interlocking vertebrae, which are classified into five segments, including (from head to tail) a cervical segment (vertebrae C1-C7), a thoracic segment (vertebrae T1-T12), a lumbar segment (vertebrae L1-L5), a sacrum segment (vertebrae S1-S5), and coccyx segment (vertebrate Co1-Co5). The cervical segment forms the neck, supports the head and neck, and allows for nodding, shaking and other movements of the head. The thoracic segment attaches to ribs to form the ribcage. The lumbar segment carries most of the weight of the upper body and provides a stable center of gravity during movement. The sacrum and coccyx make up the back walls of the pelvis.

Intervertebral discs are located between each of the movable vertebra. Each intervertebral disc typically includes a thick outer layer called the disc annulus, which includes a crisscrossing fibrous structure, and a disc nucleus, which is a soft gel-like structure located at the center of the disc. The intervertebral discs function to absorb force and allow for pivotal movement of adjacent vertebra with respect to each other.

In the vertebral column, the vertebrae increase in size as they progress from the cervical segment to the sacrum segment, becoming smaller in the coccyx. At maturity, the five sacral vertebrae typically fuse into one large bone, the sacrum, with no intervertebral discs. The last three to five coccygeal vertebrae (typically four) form the coccyx (or tailbone). Like the sacrum, the coccyx does not have any intervertebral discs.

Each vertebra is an irregular bone that varies in size according to its placement in the spinal column, spinal loading, posture and pathology. While the basic configuration of vertebrae varies, every vertebra has a body that consists of a large anterior middle portion called the centrum and a posterior vertebral arch called the neural arch. The upper and lower surfaces of the vertebra body give attachment to intervertebral discs. The posterior part of a vertebra forms a vertebral arch that typically consists of two pedicles, two laminae, and seven processes. The laminae give attachment to the ligament flava, and the pedicles have a shape that forms vertebral notches to form the intervertebral foramina when the vertebrae articulate. The foramina are the entry and exit passageways for spinal nerves. The body of the vertebra and the vertical arch form the vertebral foramen, which is a large, central opening that accommodates the spinal canal that encloses and protects the spinal cord.

The body of each vertebra is composed of cancellous bone that is covered by a thin coating of cortical bone. The cancellous bone is a spongy type of osseous tissue, and the cortical bone is a hard and dense type of osseous tissue. The vertebral arch and processes have thicker coverings of cortical bone.

The upper and lower surfaces of the vertebra body are flattened and rough. These surfaces are the vertebral endplates that are in direct contact with the intervertebral discs. The endplates are formed from a thickened layer of cancellous bone, with the top layer being denser. The endplates contain adjacent discs and evenly spread applied loads. The endplates also provide anchorage for the collagen fibers of the disc. Each disc 6 comprises a fibrous exterior surrounding an inner gel-like center which cooperate to distribute pressure evenly across each disc 6, thereby preventing the development of stress concentrations that might otherwise damage and/or impair vertebrae 4 of spinal column 2. Discs 6 are, however, subject to various injuries and/or disorders which may interfere with a disc's ability to adequately distribute pressure and protect vertebrae 4. For example, disc herniation, degeneration, and infection of discs 6 may result in insufficient disc thickness and/or support to absorb and/or distribute forces imparted to spinal column 2. Disc degeneration, for example, may result when the inner gel-like center begins to dehydrate, which may result in a degenerated disc 8 having decreased thickness. This decreased thickness may limit the ability of degenerated disc 8 to absorb shock which, if left untreated, may result in pain and/or vertebral injury While pain medication, physical therapy, and other non-operative conditions may alleviate some symptoms, such interventions may not be sufficient for every patient. Accordingly, various procedures have been developed to surgically improve patient quality of life via abatement of pain and/or discomfort. Such procedures may include, discectomy and fusion procedures, such as, for example, anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF). During a discectomy, all or a portion of a damaged disc (for example, degenerated disc 8, shown in FIG. 1), is removed via an incision, typically under X-ray guidance.

As previously noted, the various implant devices and/or components thereof disclosed herein can incorporate a silicon nitride material (i.e., $Si_3N_4$ and/or chemical analogues thereof) in their construction, either in the entirety of the implant as well as components, portions, layers and/or surfaces thereof. The incorporation of silicon nitride as a component material for spinal or other implants can provide significant improvements over existing implant materials and material designs currently available, as the silicon nitride material(s) will be highly osteo-inductive and/or osteoconductive and will desirably facilitate and/or promote implant fixation to adjacent living bone surfaces, while concurrently reducing and/or inhibiting periprosthetic infection and/or bacterial adhesion to the surfaces and/or interior portions of the implant Silicon nitride ($Si_3N_4$) and its various analogs can impart both antibacterial and osteogenic properties to an implant, including to bulk $Si_3N_4$ as well as to implants coated with layers of $Si_3N_4$ of varying thicknesses. In bone replacement as well as prosthetic joint fusion and/or replacement, osseous fixation of implants through direct bone ingrowth (i.e., cementless fixation) is often preferred, and such is often attempted using various surface treatments and/or the incorporation of porous surface layers (i.e., porous Ti6Al4V alloy) on one or more bone-facing surfaces of an implant. Silicon nitride surfaces express reactive nitrogen species (RNS) that promote cell differentiation and osteogenesis, while resisting both gram-positive and gram-negative bacteria. This dual advantage of RNS in terms of promoting osteogenesis, while discouraging bacterial proliferation, can be of significant utility in a variety of implant designs.

Desirably, the inclusion of silicon nitride components into a given implant design will encompass the use of bulk silicon nitride implants, as well as implants incorporating other materials that may also include silicon nitride components and/or layers therein, with the silicon nitride becoming an active agent of bone fusion. RNS such as N2O, NO, and —OONO are highly effective biocidal agents, and the unique surface chemistries of $Si_3N_4$ facilitate its activity as an exogenous NO donor. Spontaneous RNS elution from $Si_3N_4$ discourages surface bacterial adhesion and activity, and unlike other direct eluting sources of exogenous NO, $Si_3N_4$ elutes mainly $NH_4^+$ and a small fraction of NH3 ions at physiological pH, because of surface hydrolysis and homolytic cleavage of the Si—N covalent bond. Ammonium $NH_4^+$ can enter the cytoplasmic space of cells in controlled concentrations and through specific transporters, and is a nutrient used by cells to synthesize building-block proteins for enzymes and genetic compounds, thus sustaining cell differentiation and proliferation. Together with the leaching of orthosilicic acid and related compounds, $NH_4^+$ promotes osteoblast synthesis of bone tissue and stimulates collagen type 1 synthesis in human osteoblasts. Conversely, highly volatile ammonia $NH_3$ can freely penetrate the external membrane and directly target the stability of DNA/RNA structures in bacterial cells. However, the release of unpaired electrons from the mitochondria in eukaryotic cells activates a cascade of consecutive reactions, which starts with NH3 oxidation into hydroxylamine $NH_2OH$ (ammonia monooxygenase) along with an additional reductant contribution leading to further oxidation into $NO_2$— nitrite through a process of hydroxylamine oxidoreductase. This latter process involves nitric oxide NO formation. In $Si_3N_4$, the elution kinetics of such nitrogen species is slow but continuous, thus providing long-term efficacy against bacterial colonies including mutants (which, unlike eukaryotic cells, lack mitochondria). However, when slowly delivered, NO radicals have been shown to act in an efficient signaling pathway leading to enhanced differentiation and osteogenic activity of human osteoblasts. Desirably, $Si_3N_4$ materials can confer resistance against adhesion of both Gram-positive and Gram-negative bacteria, while stimulating osteoblasts to deposit more bone tissue, and of higher quality.

Where the presence of bulk silicon nitride implant materials may not be desired and/or may be impractical for some reason, it may be desirous to incorporate modules and/or layers including silicon nitride on other materials. Silicon nitride structures and/or components can be formed using a variety of techniques, including by compressing, milling and firing silicon nitride powder, as well as by extruding silicon nitride into sheet, tube, pipe and/or thread form (which may be further processed into thread or "rope" by braiding and/or other techniques). Silicon nitride shapes may also be manufactured using subtractive manufacturing techniques (i.e., machining, milling and/or surface roughening), as well as by using additive manufacturing techniques (i.e., surface coating, brazing, welding, bonding, deposition on various material surfaces and/or even by 3D laser printing of structures). If desired, silicon nitride may even be formed using curing or other light/energy activation techniques, such as where a slurry of liquid polymer and silicon nitride particles may be UV cured to create a 3-dimensional structure and/or layer containing silicon nitride. In various embodiments, silicone nitride may be utilized in block form, in sheets, columns and bars, in cable or braided form, in mesh form, in a textured surface coating, in powder form, in granular form, in gel, in putty, in foams and/or as a surface filler and/or coating. In some cases, a surface layer of silicon nitride may be formed on an external and/or internal surface of an implant.

For example, in some embodiments it may be desirous to laser-sinter a thin layer of silicon nitride material (i.e., powder) to the surface of another material, such as PEEK or titanium. One exemplary starting micrometric powder used for laser-sintering of a $Si_3N_4$ coating in this manner could comprise a 90 wt % fraction of $Si_3N_4$ powder mixed with a 6 wt % of yttrium oxide ($Y_2O_3$) and a 4 wt % of aluminum oxide ($Al_2O_3$). If desired, a Vision LWI VERGO-Workstation equipped with a Nd:YAG laser with a wavelength of 1064 nm (max pulse energy: 70 J, peak power 17 kW, voltage range 160-500 V, pulse time 1-20 ms, spot size 250-2000 µm) can be utilized to achieve densification of successive layers of $Si_3N_4$ powder placed on a water-wet surface of a Titanium substrate in a nitrogen environment, which desirably limits $Si_3N_4$ decomposition and oxidation. In the exemplary embodiment, the Nd:YAG laser can be pulsed with a spot size of 2 mm, and driven by an applied voltage of 400 V with a pulse time of 4 ms. This operation can be repeated until a continuous thickness of 15 µm (±5 µm) is formed over an entire surface of the Titanium substrate. This process can create a wavy morphology of the ceramic/metal interface, with interlocks at the micrometer scale between metal and ceramic phases and desirably little or no diffusional transport of the Titanium element into the coating during laser sintering.

In various embodiments, the properties of the disclosed implants will desirably include improvements in one or more of the following: (1) Flexibility in manufacturing and structural diversity, (2) Strong, tough and reliable constructs, (3) Phase stable materials, (4) Favorable imaging characteristics, (5) Hydrophilic surfaces and/or structures, (6) Osteoconductive, (7) Osteoinductive, and/or (8) Anti-Bacterial characteristics.

Figure 2A:
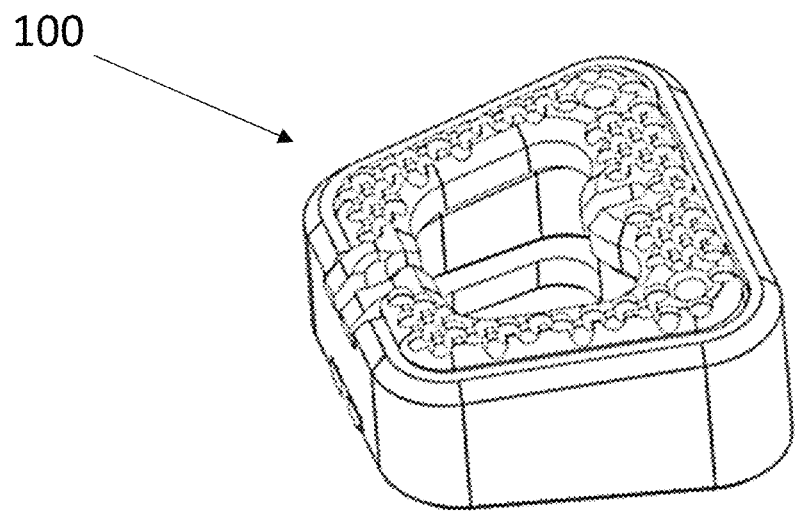
FIG. 2A illustrates a perspective view of an example of a cage structure that is constructed according to the principles of the disclosure.
Figure 2B:
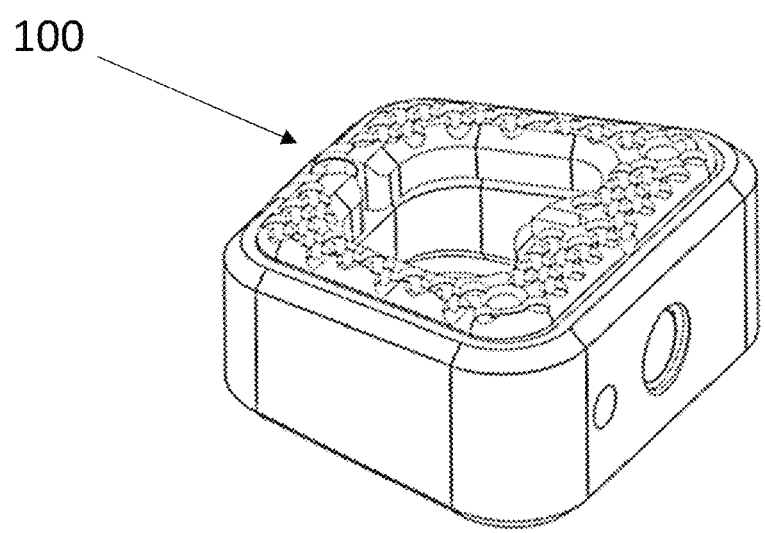
FIG. 2B illustrates another view of the cage structure illustrated in FIG. 2A.

FIGS. 2A and 2B illustrate various views of one exemplary embodiment of a cage structure 100 that can be constructed according to various principles of the disclosure, with FIG. 2A illustrating a perspective view of the cage structure 100, and FIG. 2B illustrating another view of the cage structure 100. The cage structure 100 may be constructed as one, two, three, or more parts. The cage structure 100 may comprise a silicon nitride material, which may be combined in various embodiments with other materials such as, for example, a polymer, a metal, an alloy, or the like. For instance, the cage structure 100 may comprise a central block structure made of PEEK, UHWMPE, titanium, chrome cobalt, stainless steel, a titanium alloy, or the like, with one or more outer surface layer(s) of silicon nitride to desirably increase promotion of bone growth and/or fusion in bone-contacting portions of the implant, as well as desirably reducing the potential for bacterial infection of the implant and/or the surgical site.

Figure 3:
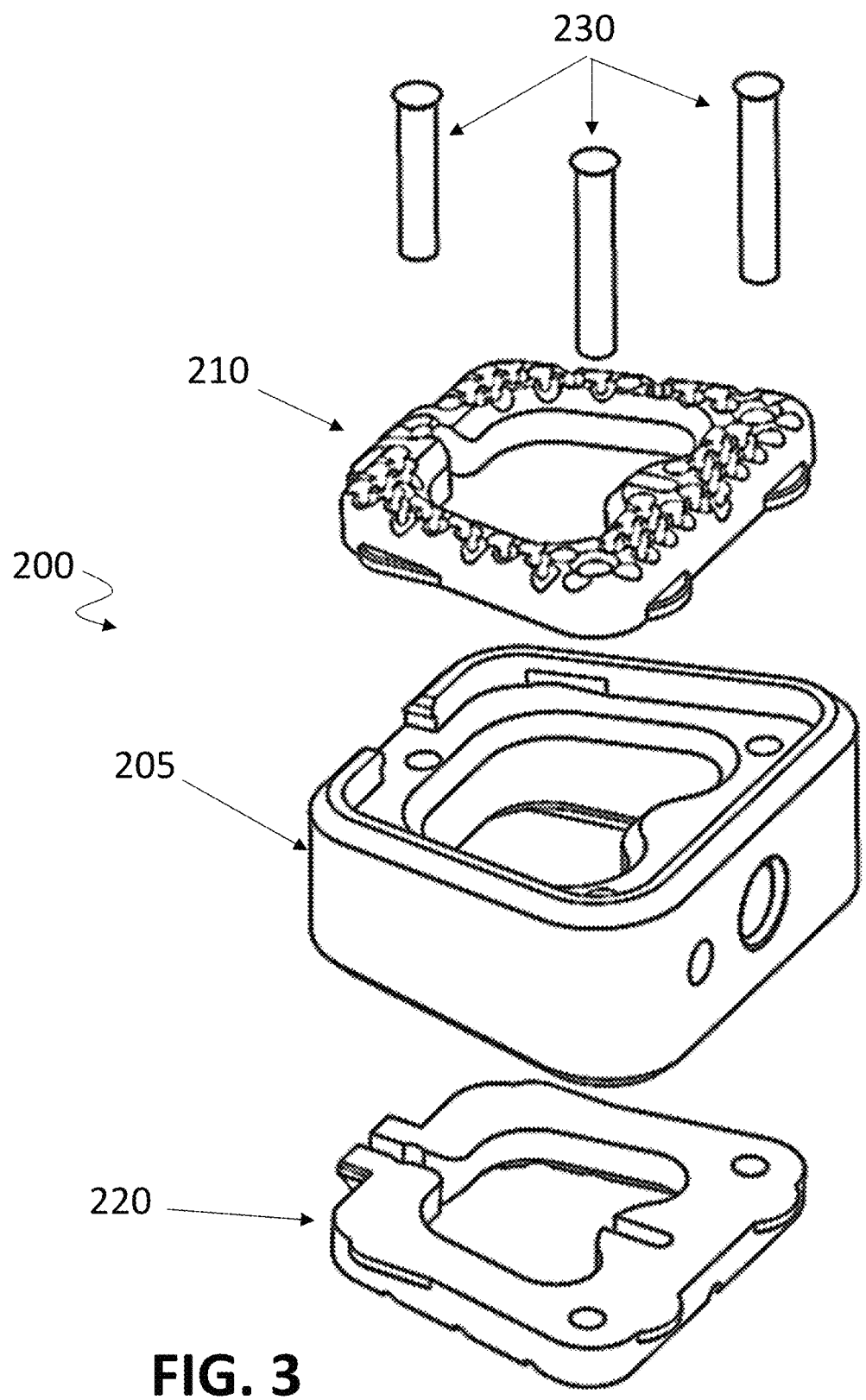
FIG. 3 depicts an exploded perspective view of one exemplary embodiment of a cage structure comprising a plurality of modular components.

FIG. 3 depicts an exploded perspective view of one exemplary embodiment of a cage structure 200 comprising a plurality of modular components. In this embodiment, a central body 205 has a modular upper surface plate 210 and a modular lower surface plate 220, wherein the various components can be secured together using pins 230 or similar securement components. If desired, the central body could comprise a PEEK material or similar material, with one or both of the modular plates 210 and 220 comprising a silicon nitride material. Alternatively, one or more of the plates 210 and 220 could comprise a titanium material having at least one externally facing surface layer of silicon nitride.

Figure 4A:
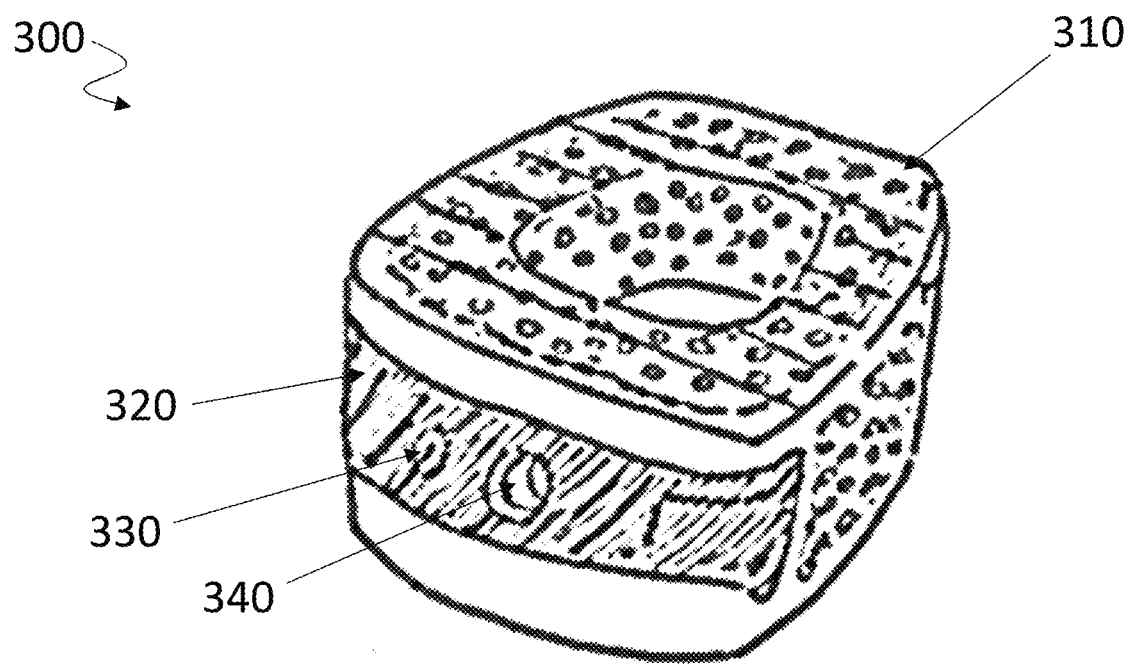
FIGS. 4A and 4B depict a perspective and top plan view of another alternative embodiment of a cage structure comprising a silicon nitride component with a supplemental component comprising a different material.
Figure 4B:
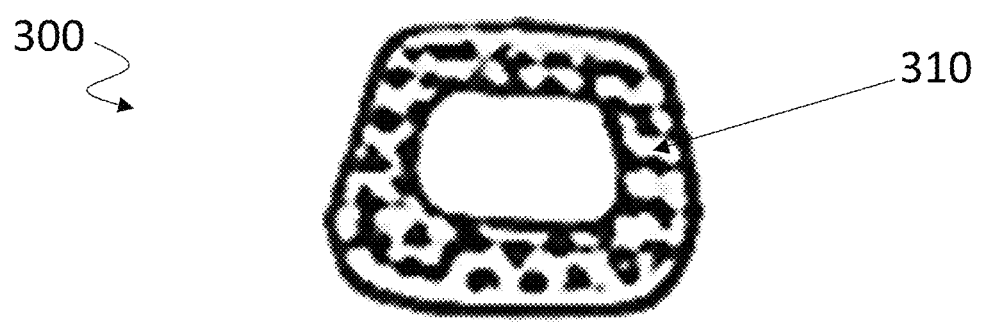

FIGS. 4A and 4B depict a perspective and top plan view of another alternative embodiment of a cage structure 300 comprising a silicon nitride component with a supplemental component comprising a different material. In this embodiment, the main body 310 of the cage structure 300 comprises a silicon nitride block, with an insert 320 comprising a metallic material such as titanium. The insert can include one or more instrument holes 330 to accommodate a surgical insertion and/or placement tool (not shown) and may also include a fixation opening 340 to accommodate a fixation screw (not shown) or removal instrument. Desirably, the insert 320 can function as a gripping point for the cage structure 300, and can also distribute impact or other loading on the silicone nitride block during insertion, adjustment and/or removal of the block in the intervertebral space.

Figure 5A:
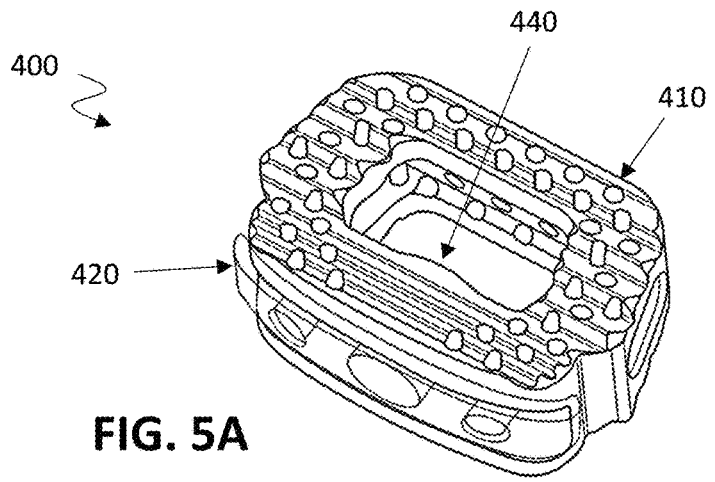
FIGS. 5A through 5D depict various views of another alternative embodiment of a cage structure comprising a porous silicon nitride body with a metallic insert.
Figure 5B:
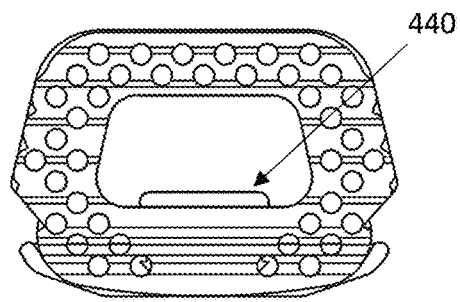
Figure 5C:
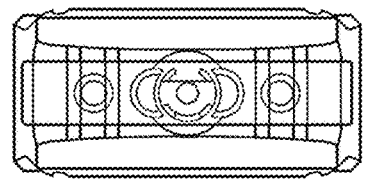
Figure 5D:
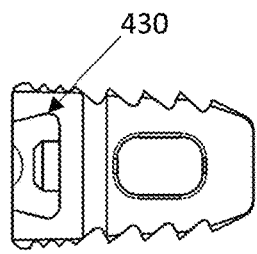
Figure 5E:
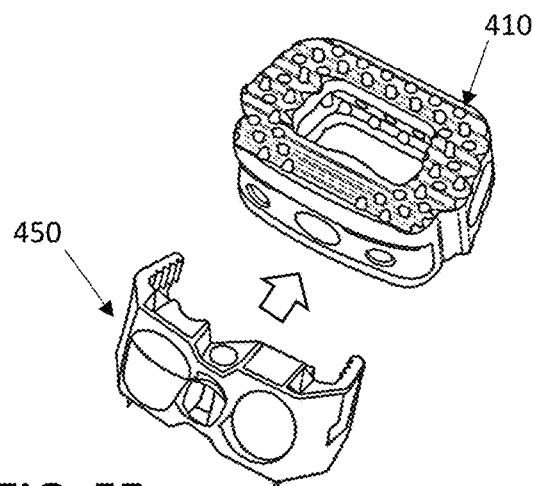
FIG. 5E depicts an alternative embodiment of an anterior plate that can be engaged with an implant body.
Figure 5F:
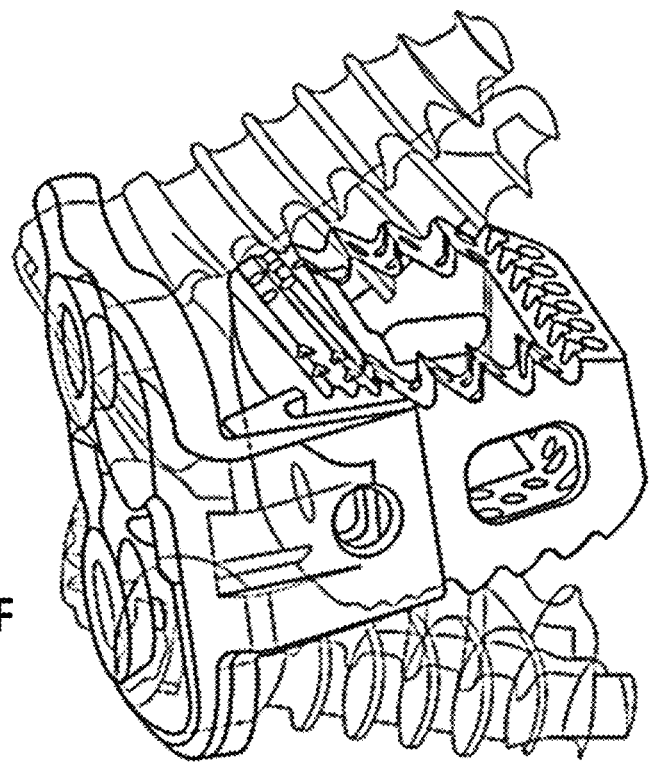
FIGS. 5F and 5G depicting alternative embodiments of implant constructs with associated fixation screws.
Figure 5G:
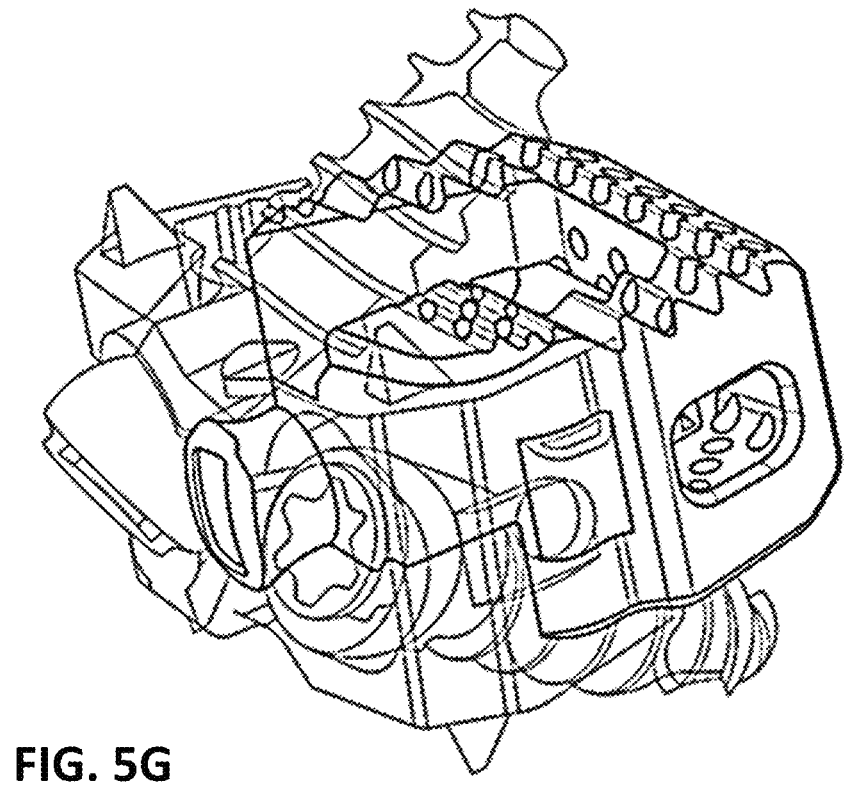
Figure 6A:
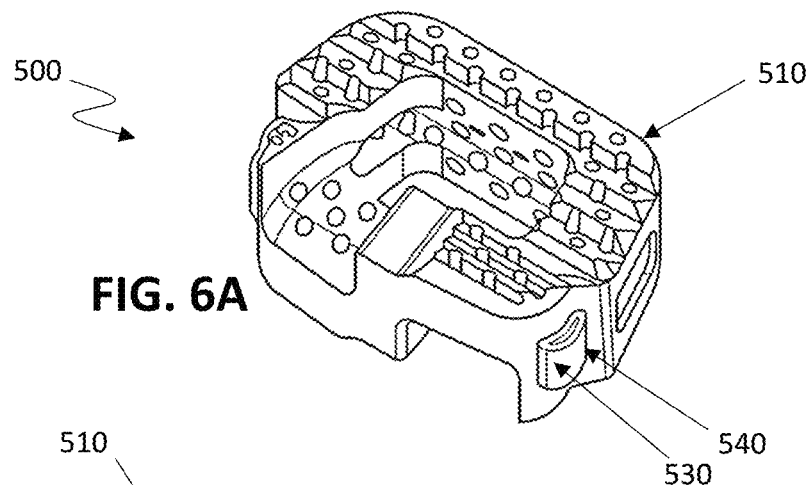
FIGS. 6A through 6D depict various views of another alternative embodiment of a cage structure comprising a porous machined silicon nitride body.
Figure 6B:
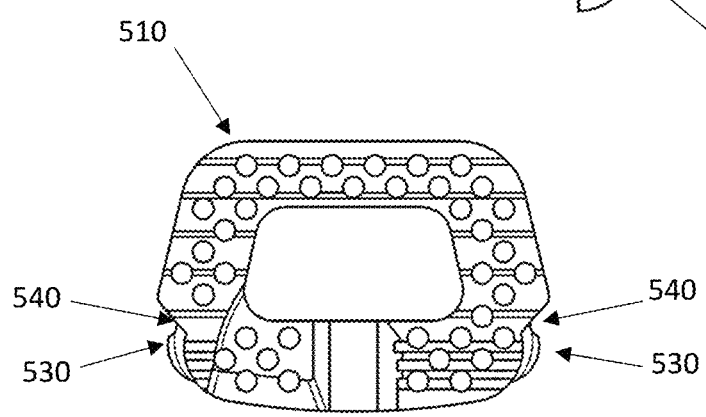
Figure 6C:
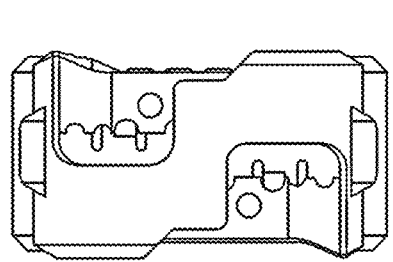
Figure 6D:
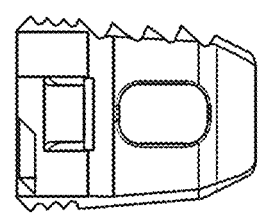

FIGS. 5A through 5D depict various views of another alternative embodiment of a cage structure 400 comprising a porous silicon nitride body 410 with a metallic insert 420. As best seen in FIG. 5D, the insert can desirably slide laterally into a dovetail slot 430 formed in an anterior portion of the body 410, and then the insert can be secured in a desired position using a fixation screw 440. In some embodiments, the fixation screw 440 can comprise an internally threaded shim, which can be utilized with a variety of surgical tools for insertion, adjustment and/or removal of the cage structure 400. FIG. 5E depicts an alternative embodiment of an anterior plate 450 that can be engaged with the body 410, if desired, with FIGS. 5F and 5G depicting various implant constructs and associated fixation screws.

FIGS. 6A through 6D depict various views of another alternative embodiment of a cage structure 500, comprising a porous machined silicon nitride body 510. In this embodiment, an anterior portion 520 of the body 510 can include one or more engagement surfaces 530 and/or engagement depressions 540, which can desirably engage with and/or accommodate one or more corresponding securement feature of an anterior plate 450 (see FIG. 5E) or similar component, which can be attached to the body 510 in a desired manner.

Figure 7A:
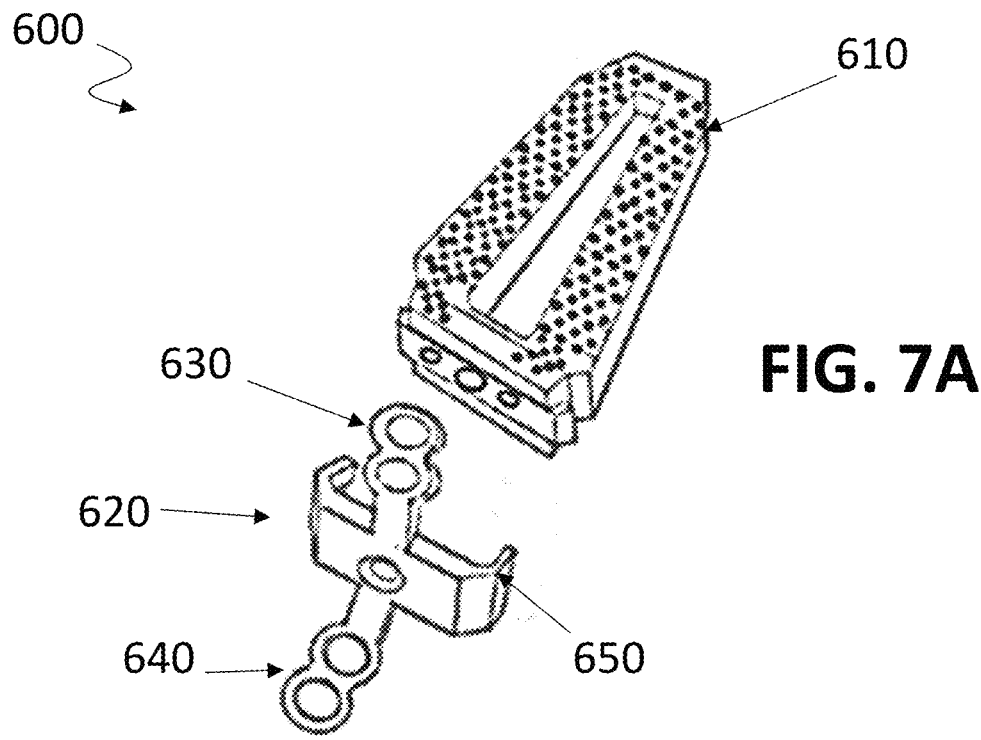
FIG. 7A depicts a perspective view of another alternative embodiment of a cage structure with a silicon nitride implant body and an anterior engagement plate.
Figure 7B:
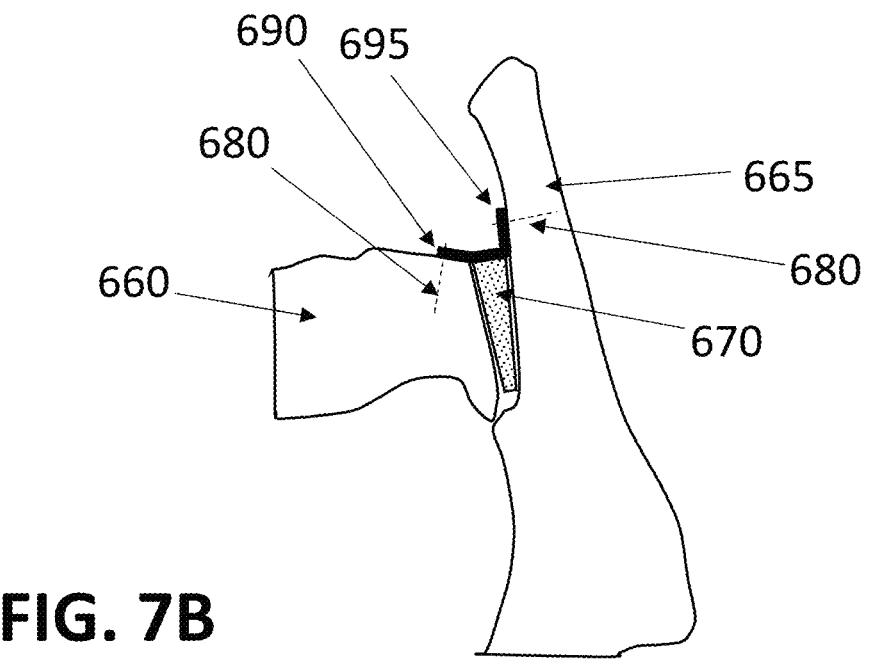
FIG. 7B depicts a cross-sectional view of a sacrum and an ilium, with the cage structure of FIG. 7A implanted therebetween.

FIG. 7A depicts a perspective view of another alternative embodiment of a cage structure 600, with a silicon nitride implant body 610 and an anterior engagement plate 620. This embodiment, which may be particularly well suited for use in sacral-iliac surgical procedures, can include one or more malleable and/or flexible elements 630, 640, and in some embodiments may optionally include a malleable plate body 650 or portions thereof. FIG. 7B depicts a cross-sectional view of a sacrum 660 and an ilium 665, with one exemplary cage structure 670 implanted therebetween. In this embodiment, the cage is anchored with fixation screws 680 into the underlying bone, with malleable elements 690 and 695 adjusted to match the underlying anatomical surfaces of the adjacent sacrum and ilium into which they are anchored.

Figure 8A:
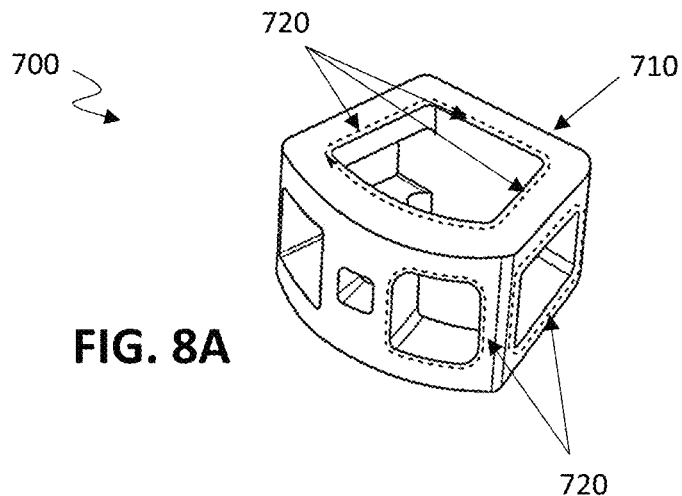
FIG. 8A depicts a perspective view of another alternative embodiment of a cage structure with a silicon nitride implant body and a plurality of support wires or walls.
Figure 8B:
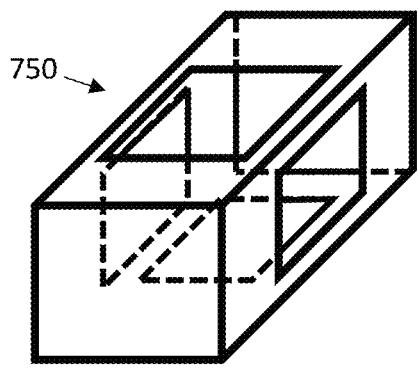
FIG. 8B depicts an exemplary wireframe-type structure.
Figure 8C:
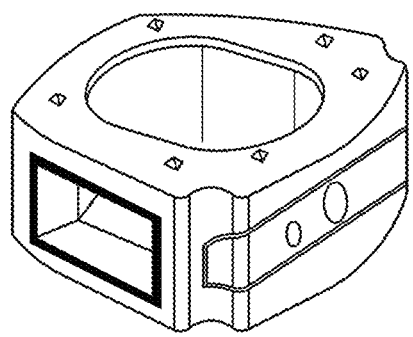
FIG. 8C depicts a supporting wall or filament support structure provided proximate to a fusion visualization window.

FIG. 8A depicts a perspective view of another alternative embodiment of a cage structure 700, with a silicon nitride implant body 710 and a plurality of support wires or walls 720 which can provide supplemental support to the implant body 710. In his embodiment, the walls 720 (indicated as dotted lines in FIG. 8A) can comprise individual filaments, wires, tubes and/or planar support structures added to the body 710 after formation of the body, or the walls can optionally comprise a wireframe-type structure 750 (i.e., a 2 or 3 dimensional wireframe structure) which may be formed prior to, during and/or after the body is formed. In such a case the wireframe could comprise a framework (see FIG. 8B) upon which a silicon nitride precursor may be positioned and/or deposited, with final firing and/or other treatment of the material may be performed to create a final implant. In various embodiments, walls or filaments or similar support structures can be provided proximate to and/or around various openings in the implant body, including around fusion visualization windows (i.e., at the medial and/or lateral sides of the body—See FIG. 8C) or around some portion or all of the central graft opening.

In other exemplary embodiments, silicon nitride materials of differing compositions and/or states (i.e., solid, liquid and/or flowable or moldable "slurry" states, for example) could be utilized in a single implant and/or portions thereof, including the use of solid silicon nitride for an arthroplasty cage implant, with a moldable silicon nitride "paste" placed within a centrally positioned "graft chamber" of the implant.

Figure 9A:
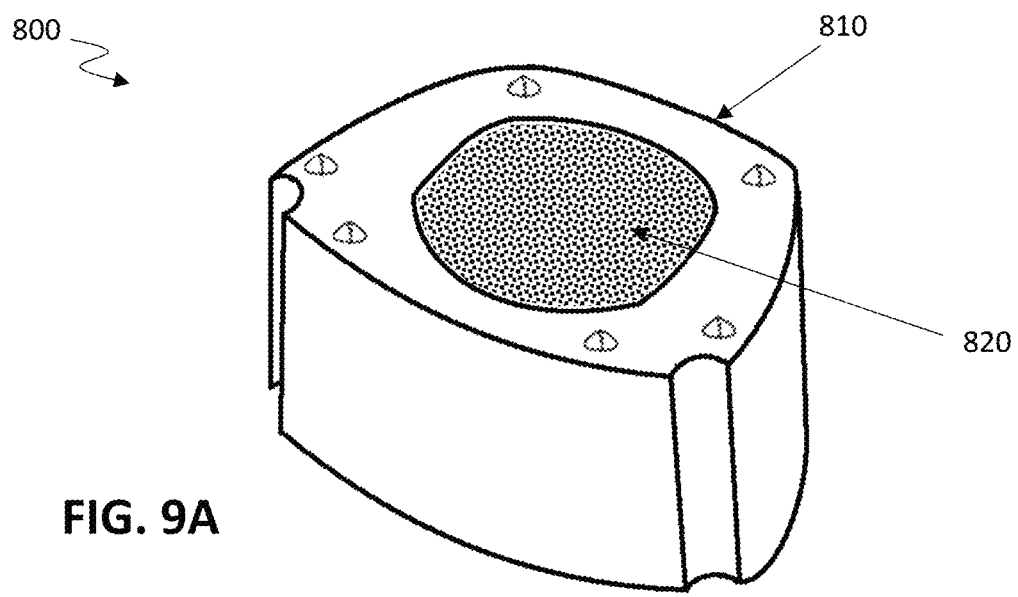
FIG. 9A depicts another exemplary embodiment of a cage structure with a silicon nitride or PEEK implant body and a silicon nitride plug.
Figure 9B:
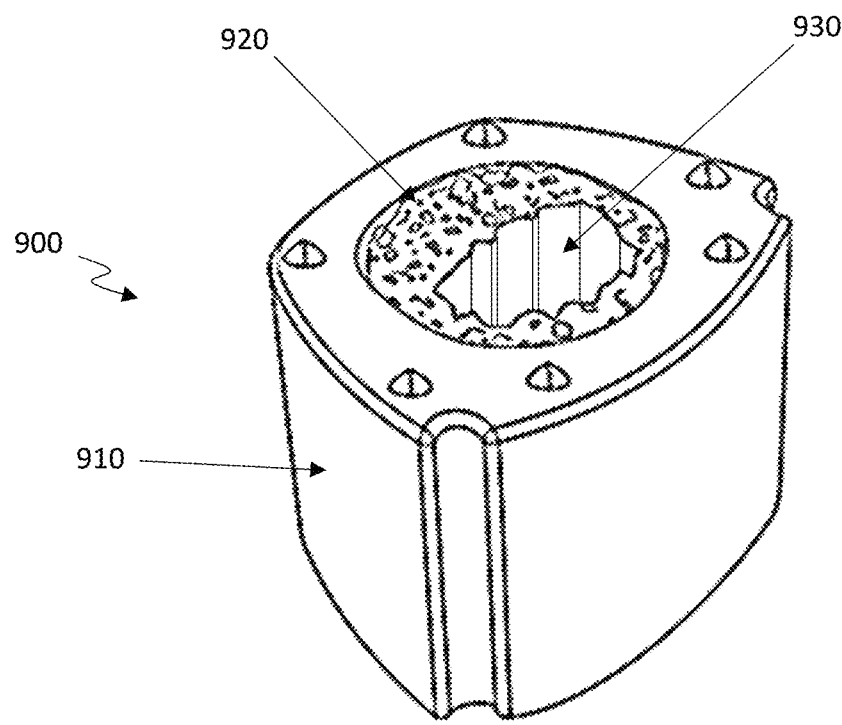
FIG. 9B depicts an alternative embodiment of a cage structure including a silicon nitride or PEEK or titanium implant body with a hollow cylinder positioned in a central cavity.
Figure 9C:
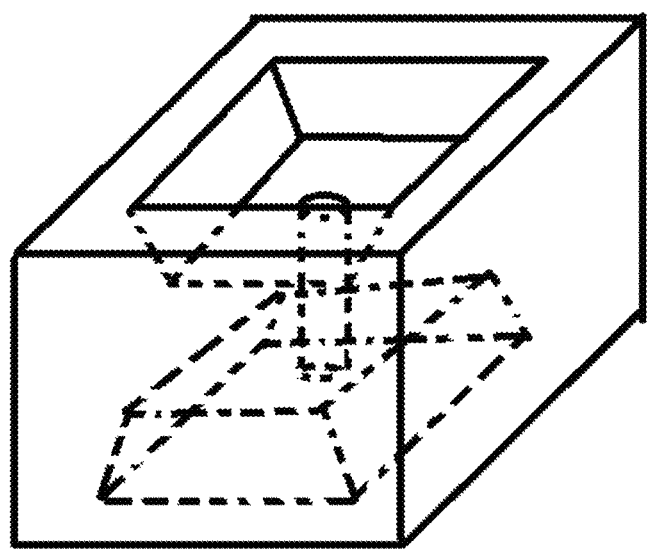
FIG. 9C depicts another alternative embodiment of a cage structure including at least one recess.

FIG. 9A depicts another exemplary embodiment of a cage structure 800, with a PEEK implant body 810 (or alternatively a silicon nitride body or portions thereof), wherein a silicon nitride plug 820 is positioned in a central cavity of the body 810. If desired, the plug 820 may be formed from a monolithic solid block of silicon nitride, or the plug could comprise a putty or gel containing silicon nitride. In another embodiment shown in FIG. 9B, the cage structure 900 includes a PEEK or titanium implant body 910 (and/or a silicon nitride body or portions thereof), with a hollow cylinder 920 positioned in a central cavity of the body 910. In this embodiment, the opening 930 in the cylinder may be further filled with bone graft or other materials, if desired. In various design alternatives, a cage structure could comprise a central block with a recess in at least one planar direction to facilitate visual of a bone graft packing area. Further alternatives could include at least one recess with a through hole (See FIG. 9C). Various geometry blocks could be made to the pre-specified inner bore geometry and height of a given commercially available implant design, with these blocks fitting into the existing implant to confer the various benefits of silicon nitrite activity thereto. The dimensions of a given silicon nitride block could be smaller than one or more dimensions of the existing implant, or the block could be tapered or straight to facilitate insertion into the implant. If desired, a silicon nitride block or similar component could extend completely through an implant, or only extend partially into and/or out of an implant. FIG. 10 depicts various cross-sectional views of a spinal implant with various exemplary silicon nitride insert geometries formed therein.

In various embodiments the disclosed implants will desirably incorporate materials such as silicon nitride that are "phase stable" to a desired degree. For example, Various embodiments will desirably withstand standard autoclave sterilization conditions such as 120° C. 1 atmosphere steam for up to 100 hours of time, with no appreciable change in phase composition, no appreciable change in flexural strength and an inherently stable microstructure. Moreover, such materials will desirably provide favorable imaging characteristics, such as high levels of radiolucency and/or no significant MRI or CT scan artifacts.

Figure 11:
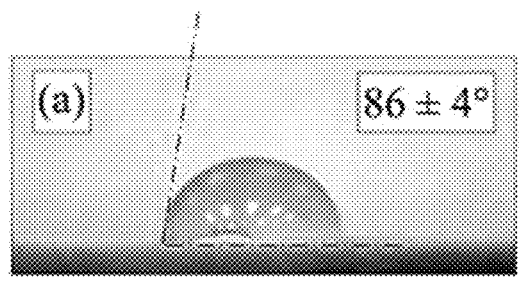
FIG. 11 depicts exemplary degrees of hydrophobicity for various medical grade materials, including silicon nitride.
Figure 11:
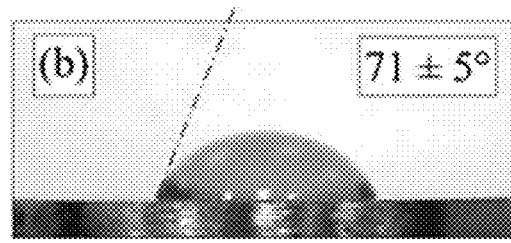
Figure 11:
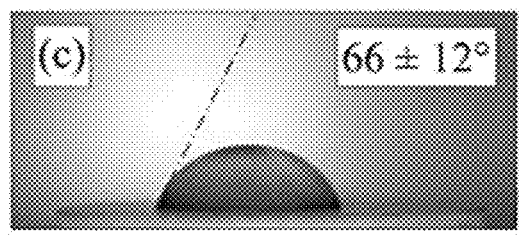
Figure 11:
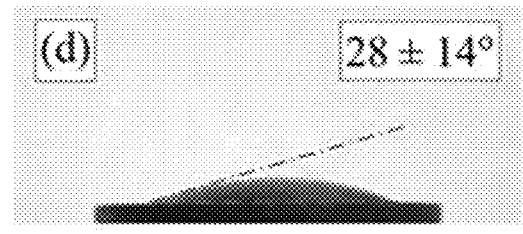
Figure 11:
Figure 11:
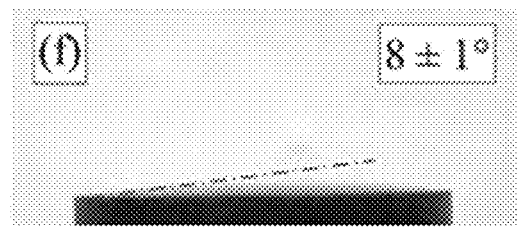
Figure 12A:
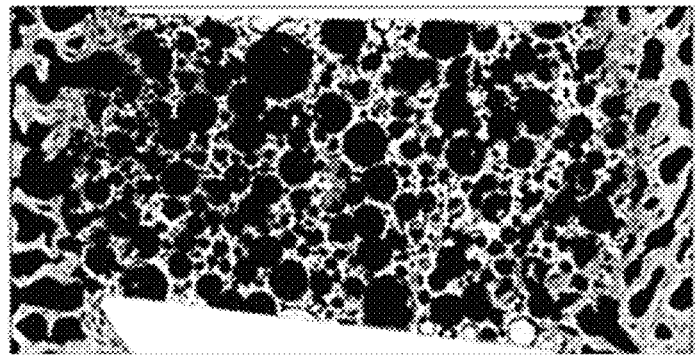
FIGS. 12A and 12B depict cross-sectional views of silicon nitride implants with neovascularization induced within the porous sections of the implant.
Figure 12B:
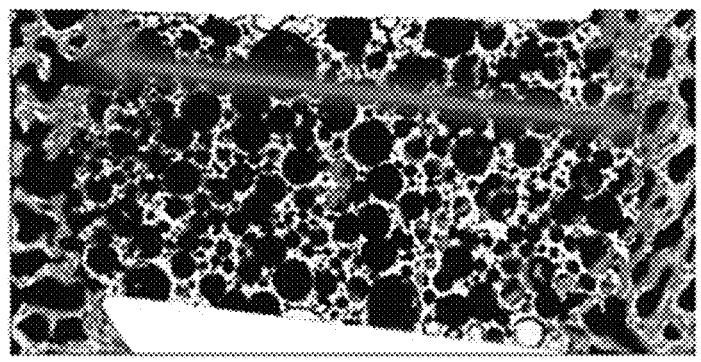

FIG. 11 depicts exemplary degrees of hydrophobicity for various medical grade materials, including silicon nitride in various forms utilized herein. As shown, silicon nitride is much less resistant to water penetration than other materials, which can be a highly desirably characteristic in many applications. In many applications, a porous implant formed from silicon nitride can induce neovascularization within the porous sections of the implant, including internal pores colonized with mineralized bone to a depth exceeding 5.5 mm, such as depicted in FIGS. 12A and 12B.

Figure 13A:
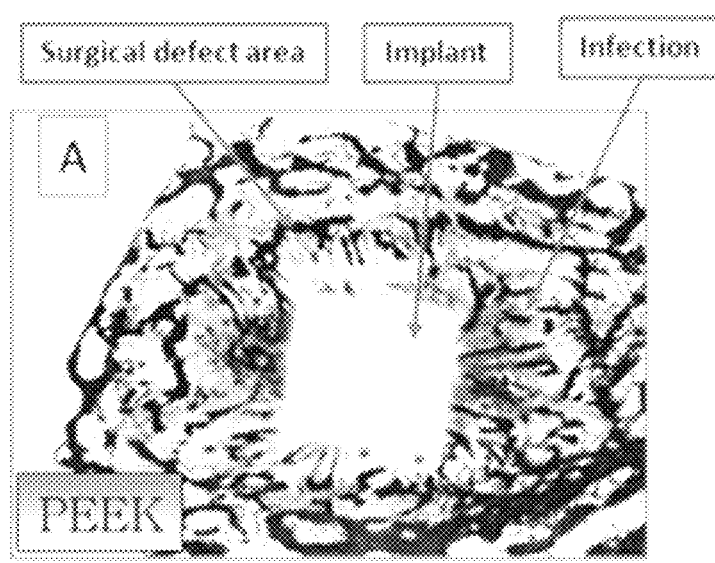
FIGS. 13A through 13C depict three exemplary implants made of PEEK, Titanium and silicon nitride and their effects on adjacent living bone.
Figure 13B:
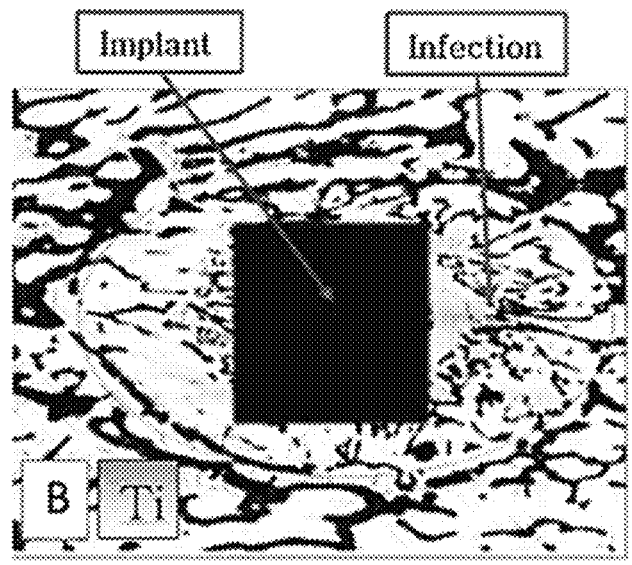
Figure 13C:
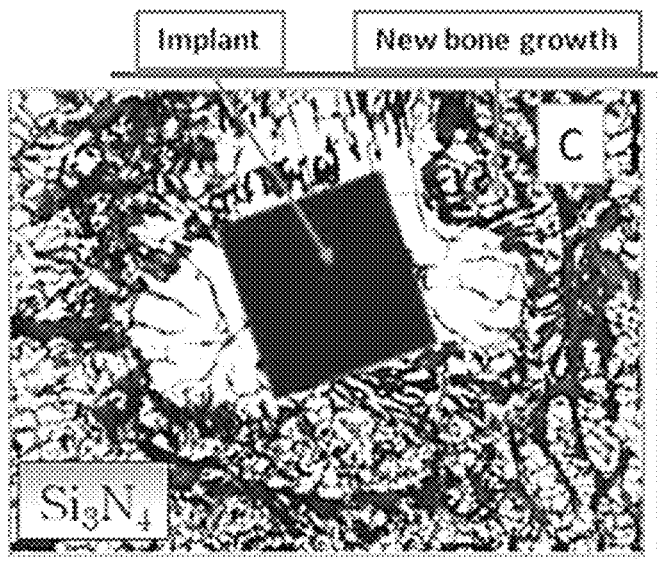
Figure 13D:
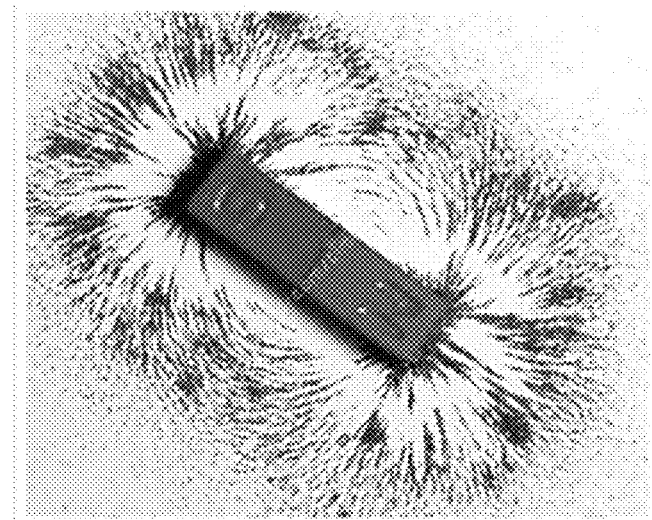
FIG. 13D depicts a magnetic field induced by a bar-type magnet.
Figure 13E:
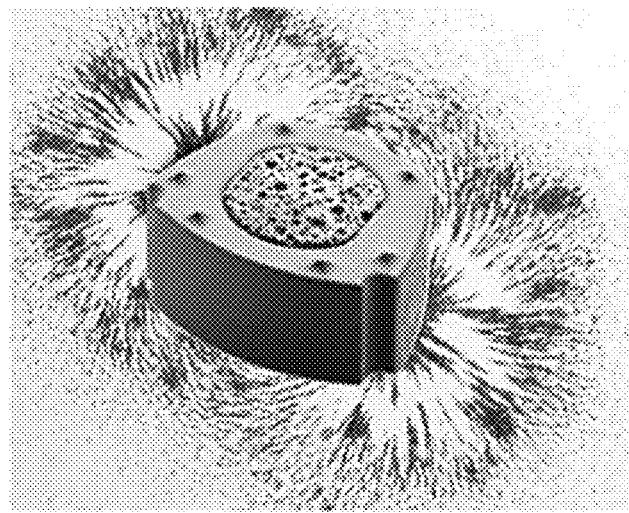
FIG. 13E depicts the effect of silicon nitride material on new bone growth.

FIGS. 13A through 13C depict three exemplary implants made of PEEK, Titanium and silicon nitride and their effects on adjacent living bone. As shown in FIG. 13A, a PEEK implant may often be accompanied by surgical bone defects that do not fill in with new bone over time, as well as potential infection sites proximate to the implant that may be difficult or impossible to resolve (potentially necessitating implant removal in some cases). In a similar manner, as shown in FIG. 13B, bone infection sites near titanium implants can also be difficult or impossible to resolve, and may similarly necessitate implant removal. However, with a silicon nitride implant, such as shown in FIG. 13C, the surface chemistry of the implant actively destroys infectious bacterial agents, and also induces new bone growth immediately upon implantation. In essence, the effect of the silicon nitride material on new bone growth acts like a magnet on ferrous materials (see FIG. 13D), actively "drawing" new bone near and into the implant (see FIG. 13E).

Another significant advantage of using silicon nitride materials in bone implants is the anti-bacterial effects of the material on infectious agents. As best seen in FIG. 14A, upon implantation a silicon nitride surface can induce an inflammatory response action which attacks bacterial biofilms near the implant. This reaction can also induce the elevation of bacterial pods above the implant surface by fibrin cables (see FIG. 14B). Eventually the bacteria in the vicinity of the silicon nitride implant surfaces will be cleared by macrophage action, along with the formation of osteoblastic-like cells (See FIG. 14C). In various experiments involving comparisons between standard implants and silicon nitride implants (both bulk and silicon nitride coated implants of standard materials), cell viability data in (which were determined at exposure times of 24 and 48 hours, showed the existence of a larger population of bacteria on the standard medical materials as compared to $Si_3N_4$ implants (both coated and bulk). A statistically validated decreasing trend for the bacterial population with time was detected on both coated and bulk substrates, with a highest decrease rate on $Si_3N_4$-coated substrates. Moreover, the fraction of dead bacteria at 48 h was negligible on the standard implants, while almost the totality of bacteria underwent lysis on the $Si_3N_4$ substrates. In addition, optical density data provided a direct assessment of the high efficacy of the $Si_3N_4$ surfaces in reducing bacterial adhesion.

In various embodiments, silicon nitride materials can be incorporated into a variety of implants and implant-like materials, including (1) orthopedic bone fusion implants (i.e., screws, cages, cables, rods, plugs, pins), (2) dental implants, (3) cranial/maxillofacial implants, (4) extremity implants, (5) hip and joint implants, (6) bone cements, powders, putties, gels, foams, meshes, cables, braided elements, and (7) bone anchoring elements and/or features. Where a surface coating of silicon nitride is added to an existing implant, such as to a titanium implant using a 3D-laser-sintering manufacturing process of deposition, this surface coating may comprise a dense, tenaciously adherent $Si_3N_4$ coating (with thickness 10-20 μm) onto the porous T-alloy surface of commercially available components, which may achieve rapid osseous fixation, while resisting bacteria.

Because many forms of silicon nitride exhibit ceramic-like mechanical properties, these materials may not be well suited for use in screws that may be more than 4 mm in diameter and 15 mm in length, which can be subject to various brittleness failures when inserted into a bone. For spinal applications, where bigger diameter screws such as up to 10.5 mm in diameter and lengths up to 120 mm long may be required, more traditional implants of metal may be desirous for implantation, such as to overcome friction and hardness of human/animal bone. Thus, a typical screw consisting of a single material, screw head, threaded shaft, and tapered tip with cutting flutes may desirably be reconfigured where the threaded shaft portion is partially made of a bone-growth enhancing non-metallic material such as a silicon nitrate, particularly on the surface where it contacts the bone. Various methods to integrate such component can be used, such as making a threaded sleeve of silicon nitrate material. Many methods for assembling such a design can be utilized, such as employing a horseshoe shaped sleeve which engages around a single piece central column of a pedicle screw. In various alternative embodiments, a threaded cannulated sleeve could be provided, with or without external and/or internal threaded features, and even where the base screw head and/or shaft with tip could comprise multiple components and/or multiple materials to make the assembly functional and durable. In some embodiments, a surface of the sleeve component could be configured with patterns and/or textures to further increase the surface area of bone contact within a pre-tapped hole in the bone.

Figure 15A:
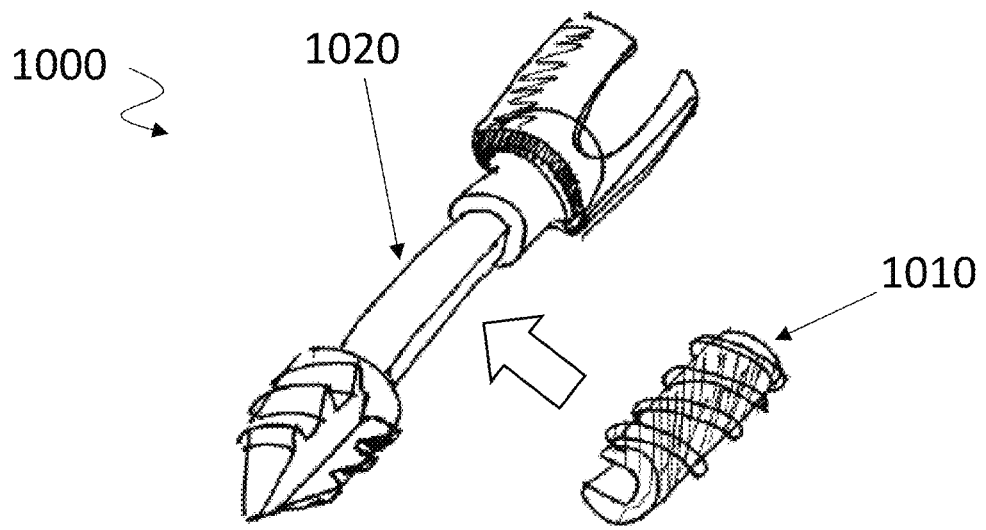
FIGS. 15A and 15B depict views of another exemplary embodiment of a surgical implant that incorporates silicon nitride features to enhance osseous integration and/or improve bacterial resistance.
Figure 15B:
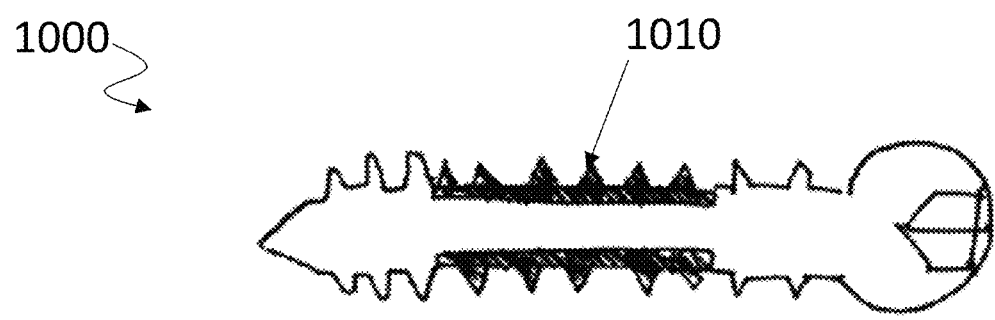

FIGS. 15A and 15B depict another exemplary embodiment of a surgical implant that incorporates silicon nitride features to enhance osseous integration and/or improve bacterial resistance. In this embodiment, a bone growth enhancing screw 1000 is provided, the screw having a screw body 1005 and a modular threaded sleeve 1010 that can be placed onto a central shaft 1020 of the screw body 1005. Desirably, the screw body 1005 will comprise a metallic material such as titanium, which is a commonly accepted and highly tested medical material for bone screws. However, because metal bone screws may not contribute significantly to osseous fixation, the sleeve can comprise a material such as silicon nitride or similar materials that desirably induce osseous integration. Such an arrangement allows silicon nitride to be integrated into the metal bone screw without sacrificing significant strength and/or durability of the screw. Alternatively, a coating of silicon nitride could be applied to one or more surfaces of the bone screw (i.e., through a laser sintering or other method), as previously described. In various alternative embodiments, $Si_3N_4$ powder may be laser sintered to titanium or PEEK base materials.

In various embodiments, silicon nitride can be manufactured into various shapes and/or sizes, and can be attached to a shaft or other feature of a bone screw as described herein. Because silicon nitride may not be effective on a cutting surface, the cutting tip of the bone screw may desirably comprise a metal cutting tip. Moreover, because the silicon nitride material may shrink or otherwise deform during portions of the manufacturing and/or curing process, it is desirable that the implant design features accommodate potential changes in the design of the insert or similar components. In at least one alternative embodiment, silicon nitride material may be manufactured in a sleeve or other shape, with the corresponding metal screw shape subsequently being modified to accommodate the final cured shape and/or size of the silicon nitride sleeve insert. In various alternative embodiments, the sleeve insert could alternatively comprise a silicon nitride tip or "washer" placed around the screw head, or silicon nitride strips, inserts or "teeth" could be provided along the longitudinal length of the screw.

Figure 16A:
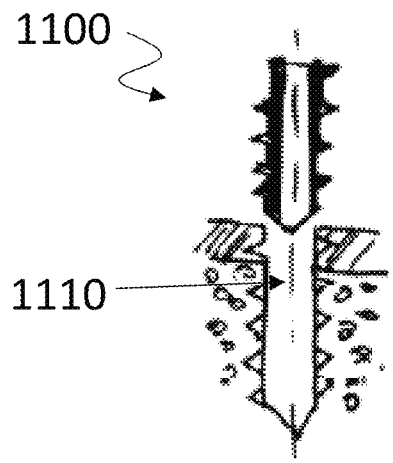
FIGS. 16A through 16E depict another exemplary embodiment of a surgical implant that incorporates silicon nitride features to enhance osseous integration and/or improve bacterial resistance.
Figure 16B:
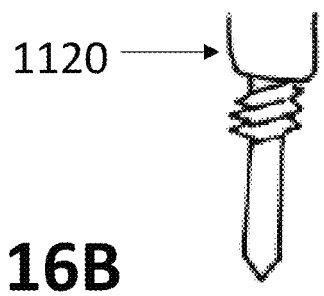
Figure 16C:
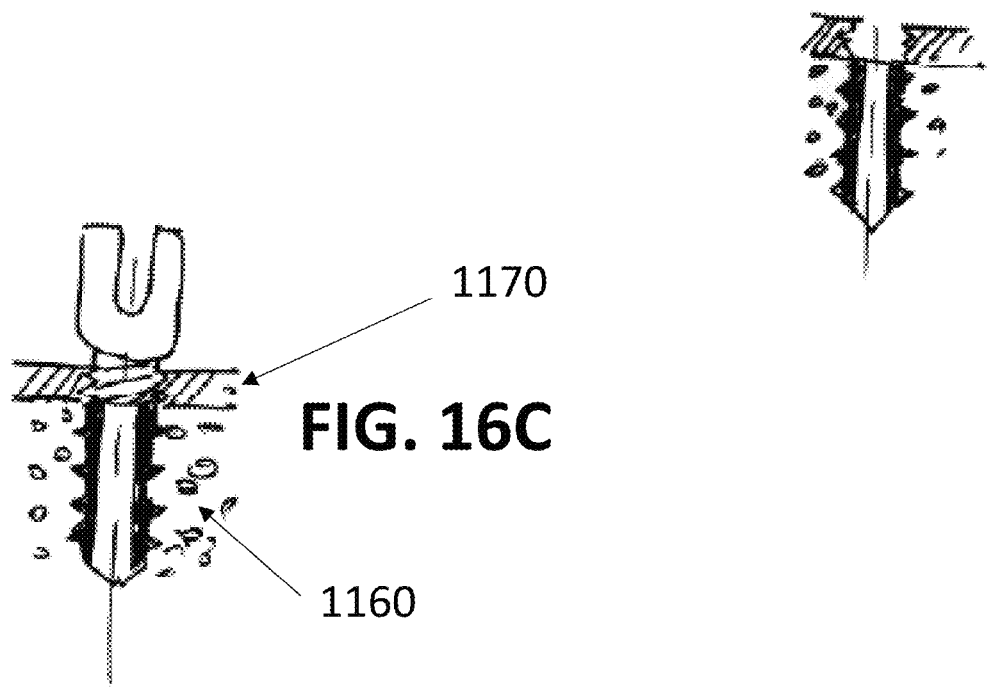
Figure 16D:
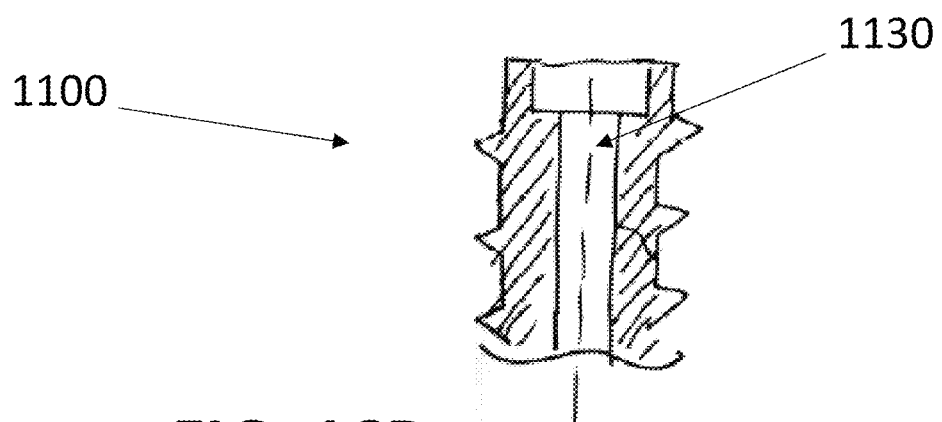
Figure 16E:
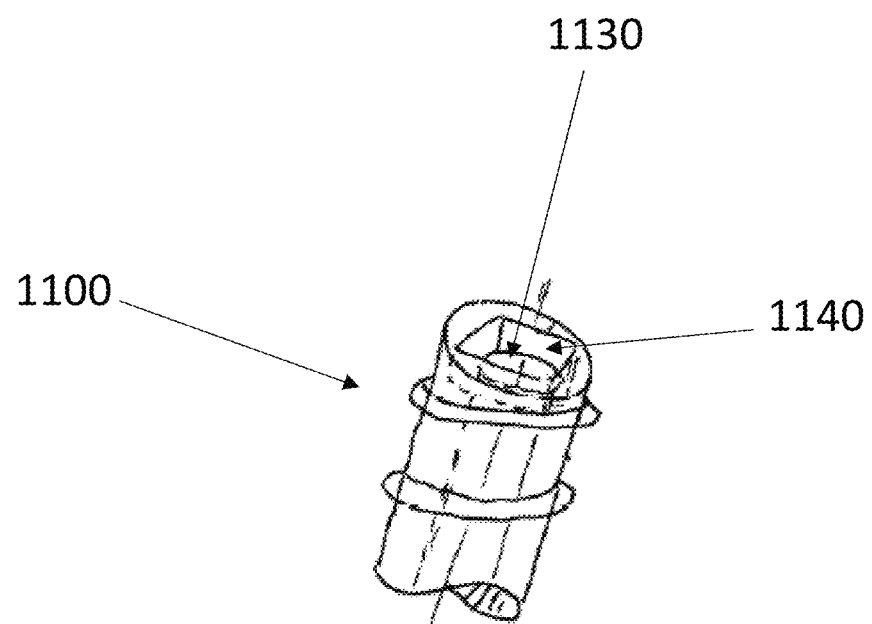

In other embodiments, such as for application to hard bone where the bone may be already tapped, a silicon nitride sleeve element with thread that spans from a screw neck region to a distal tip of a bone screw may be utilized, where the sleeve is inserted into the pre-tapped bore, then the screw body is inserted onto the former and locks axially and/or rotationally. In some embodiment, the sleeve and/or screw body could be pre-assembled and inserted simultaneously into a pre-tapped bore. FIGS. 16A through 16E depict another exemplary embodiment of a surgical implant that incorporates silicon nitride features to enhance osseous integration and/or improve bacterial resistance. In this embodiment, a silicon nitride anchor or sleeve 1100 can be inserted into a prepared hole 1110 in a patient's anatomy, and then a bone screw 1120 or similar device can be inserted into an opening 1130 through the center of the sleeve. If desired, the hole 1110 can be prepared by drilling and/or tapping, and the sleeve 1100 can be advanced into the hole 1110 in a variety of ways. If desired, the sleeve 1100 can include external and/or internal threading, as well as a driving feature 1140 (see FIG. 16E), which can allow the sleeve 1100 to be rotated using a surgical driving tool for advancement into the hole 1110. As best seen in FIG. 16D, one embodiment of a sleeve will desirably provide supplemental fixation to a cancellous region 1160 of the bone, while concurrently allowing a screw thread portion of the screw to engage with a cortical layer 1170 of the bone.

Figure 17A:
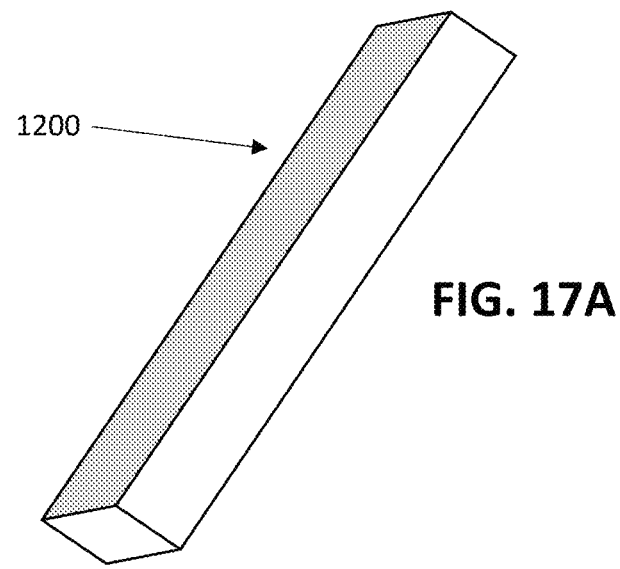
FIGS. 17A though 17G depict various views of a rotation resistant spinal rod and screw system.
Figure 17B:
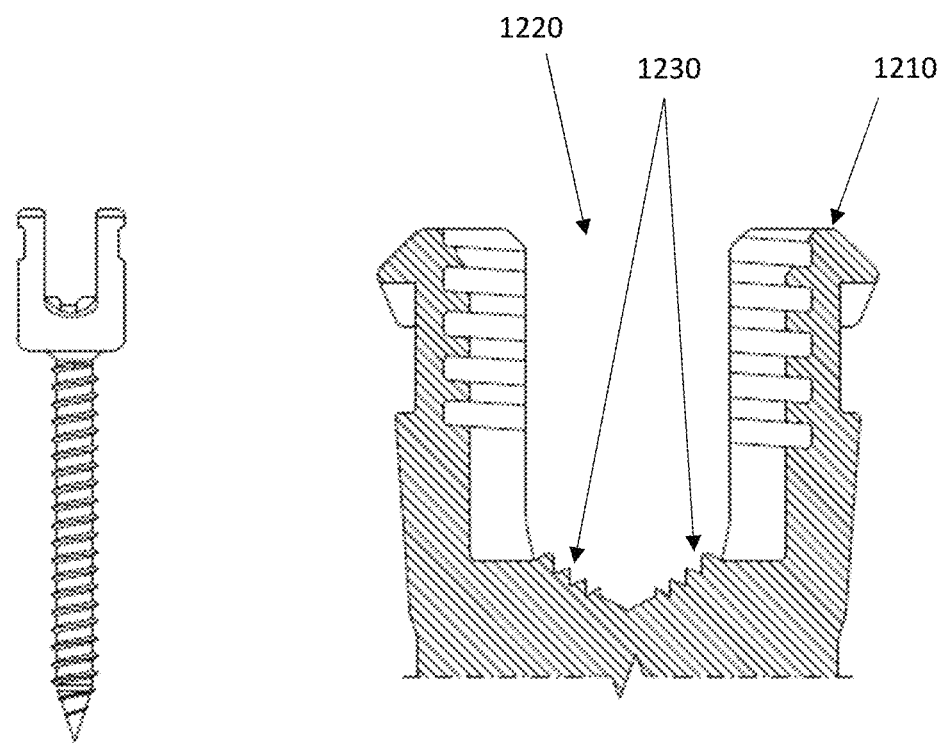
Figure 17C:
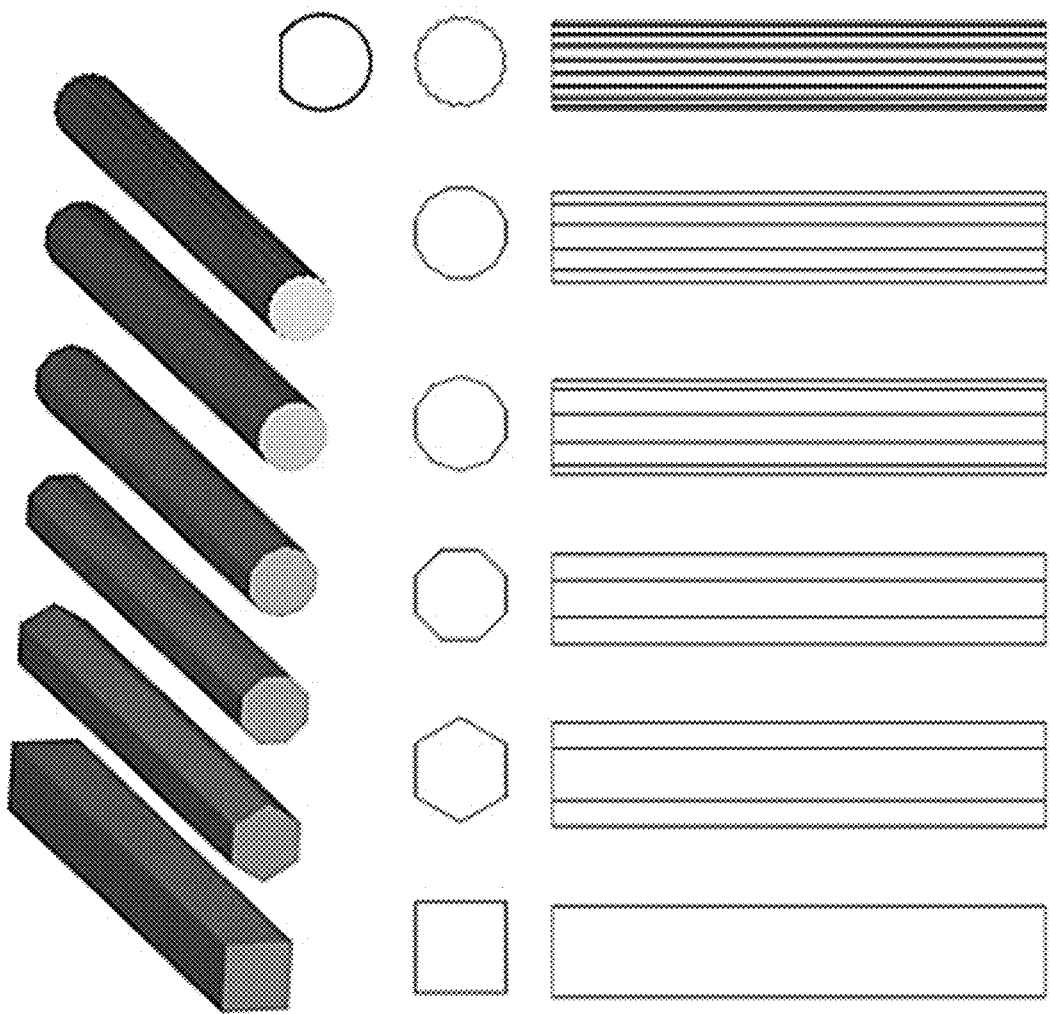
Figure 17E:
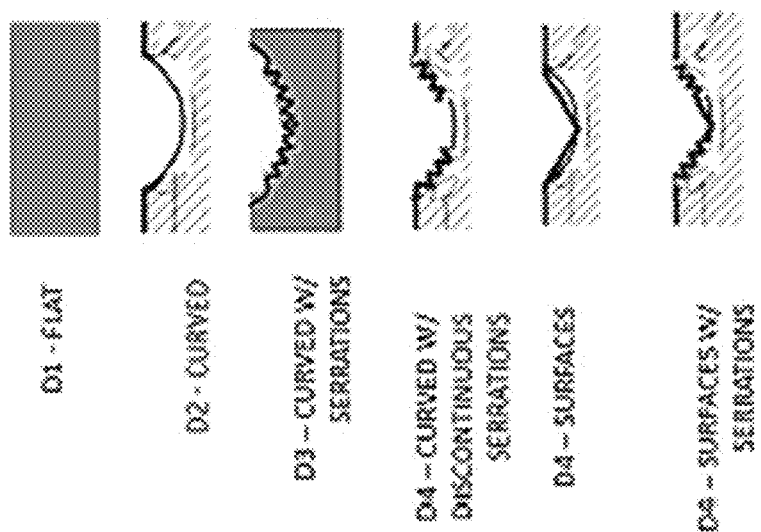
Figure 17D:
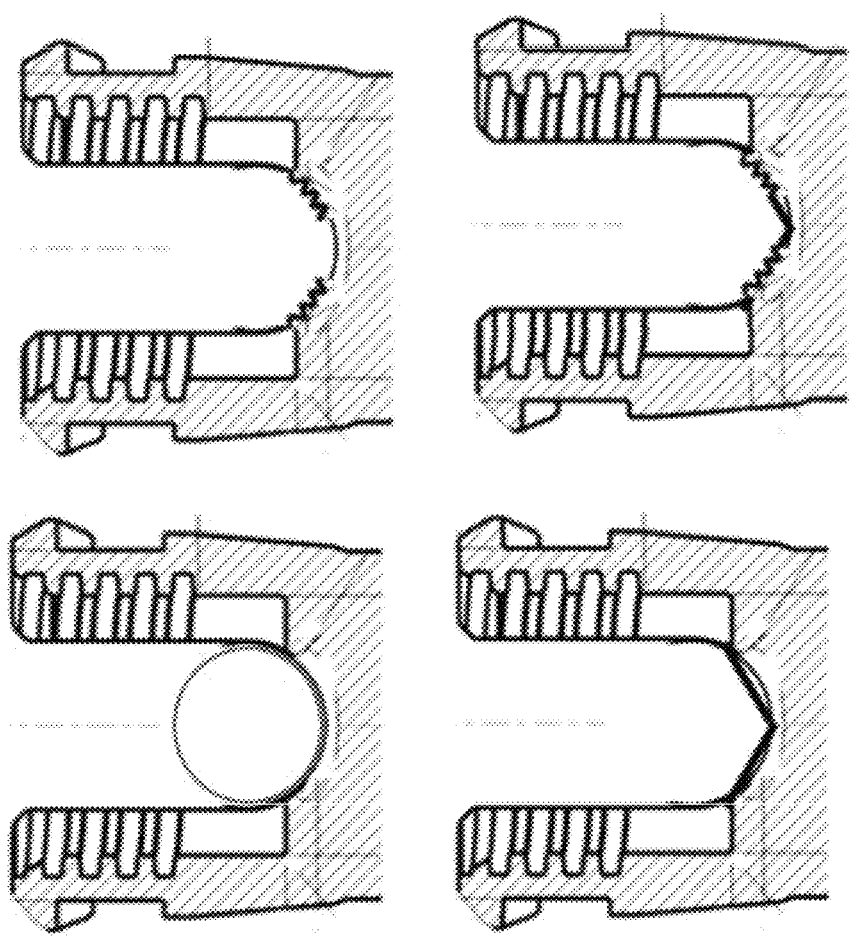

FIG. 17A depicts view of another alternative embodiment of a modular implant component for employment in surgery of the spine and other anatomical regions. In this embodiment, a connecting rod or shaft 1200 (which may optionally comprise silicon nitride in some portion thereof) is disclosed which provides improved fixation and stability to a surgical implant construct, which may be particularly useful in deformity correction and/or various types of spinal surgery. In this embodiment, the connecting rod 1200 desirably includes roughened and/or non-smooth external features, which can include a variety of polygonal shapes such as square and/or hexagonal rods surfaces, which desirably interact with a corresponding screw head such as depicted in FIG. 17B. The screw head 1210 desirably includes a generally U-shaped saddle or receptacle 1220 which includes one or more engagement features 1230 for engaging with external portions of the shaft 1200, desirably inhibiting and/or preventing rotation of the shaft within the screw head. FIG. 17C depicts shaft of varying configurations, FIG. 17D depicts corresponding screw heads of varying configurations, and FIG. 17E depicts various alternative engagement features.

Figure 17F:
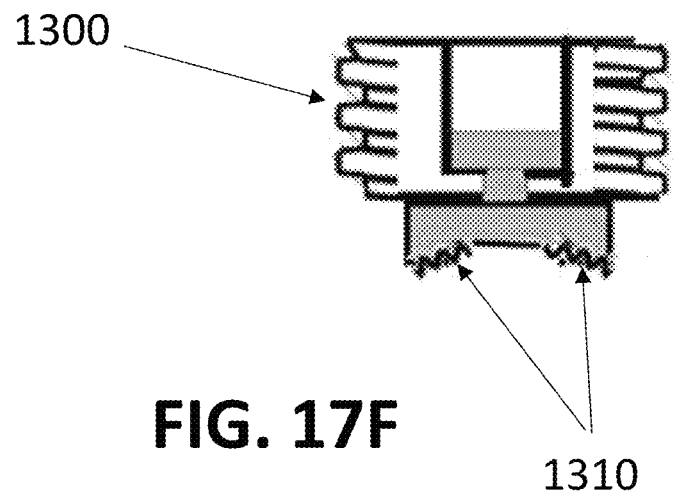
Figure 17G:
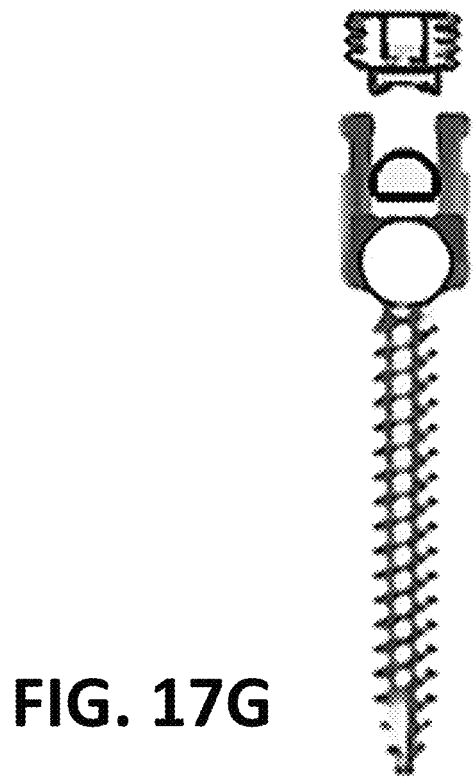

FIG. 17F depicts a cross-sectional view of a tightening screw or set screw 1300, which can be utilized to secure a connecting shaft to a screw head. In this embodiment, the set screw includes one or more engagement features 1310 for engaging with external portions of the shaft 1200, desirably inhibiting and/or preventing rotation of the shaft within the screw head. FIG. 17G depicts an exemplary screw and rod assembly.

In various embodiments, a surgical tool kit could include an implant and one or more modular components for the system, including individual silicon nitride components or a modular replacement, if desired. The various components of these systems could optionally be provided in kit form, with a medical practitioner having the option to select an appropriately sized and/or shaped implant and/or modular components to address a desired surgical situation.

Note that, in various alternative embodiments, variations in the position and/or relationships between the various figures and/or modular components are contemplated, such that different relative positions of the various modules and/or component parts, depending upon specific module design and/or interchangeability, may be possible. In other words, different relative adjustment positions of the various components may be accomplished via adjustment in separation and/or surface angulation of one of more of the components to achieve a variety of resulting implant configurations, shapes and/or sizes, thereby accommodating virtually any expected anatomical variation. For example, variation of the thicknesses and/or separation distance between various surfaces (i.e., optionally without altering the angulation of the surfaces) can desirably cause an increase or decrease in the size or "height" of the implant, due to changes in the z-axis positioning of the components which engage the adjacent vertebrae. Concurrently, alterations in the "tilt angle" or angulation of one or both of the surfaces or other components in the medial-lateral (i.e., rotation about a y-axis) and/or anterior-posterior (i.e., rotation about an x-axis) axes of the implant will allow the implant to be utilized to accommodate a wide variety of natural and/or surgically altered surfaces of the spine. Moreover, various complex combinations (at various amounts) of comparative lateral (e.g., left-right) tilt and fore-aft (e.g., anterior-posterior) tilt can be accomplished, with or without concurrent adjustments in the various cutting surfaces.

The various embodiments of an implant disclosed herein can be configured to interact with two bone vertebrae of a spine or other anatomical locations. The spine may have any of several types of spinal curvature disorders which are sought to be treated. Examples of such spinal curvature disorders include, but need not be limited to, lordosis, kyphosis, scoliosis and/or low and/or high velocity fractures, among other pathologies.

In various exemplary scenarios, a variety of surgical tools can be used in conjunction with various implant devices utilized to fix and/or secure adjacent vertebrae that have had cartilaginous disc between the vertebrae replaced with fusion material that promotes the fusion of the vertebrae, such as a graft of bone tissue. Also, such can be accomplished even when dealing with a spinal curvature disorder (e.g., lordosis, kyphosis and scoliosis).

Of course, method(s) for manufacturing the surgical devices and related components and implanting an implant device into a spine are contemplated and are part of the scope of the present application.

While embodiments and applications of the present subject matter have been shown and described, it would be apparent to those skilled in the art that many more modifications are possible without departing from the inventive concepts herein. The subject matter, therefore, is not to be restricted except in the spirit of the appended claims.

All references, including publications, patent applications, and patents, cited herein are hereby incorporated by reference to the same extent as if each reference were individually and specifically indicated to be incorporated by reference and were set forth in its entirety herein.

The various headings and titles used herein are for the convenience of the reader and should not be construed to limit or constrain any of the features or disclosures thereunder to a specific embodiment or embodiments. It should be understood that various exemplary embodiments could incorporate numerous combinations of the various advantages and/or features described, all manner of combinations of which are contemplated and expressly incorporated hereunder.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., i.e., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventor for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An interbody system for implanting between vertebrae, comprising:

a cage having a cage body wherein at least a first portion of the cage body comprises a silicon nitride material and a second portion of the cage body comprises at least one material from the group consisting of titanium, chrome cobalt, stainless steel, silicone, poly (ether ether ketone) (PEEK), ultra-high molecular-weight polyethylene (UEMWPE), polyurethane foam, polylactic acid and apatite, the cage body including a graft chamber; and
a moldable graft material placed within the graft chamber, the moldable graft material comprising a silicon nitride paste, and
a sagittal wall that forms a portion of the graft chamber.

2. The interbody system of claim 1, wherein the cage body further comprises an anterior plate attached to the cage body by at least one fixation screw.

3. The interbody system of claim 1, wherein the at least a first portion of the cage body comprises a morselized form of silicon nitride material.

4. The interbody system of claim 1, wherein at least a portion of the cage body is porous.

5. The interbody system of claim 2, wherein at least a portion of the anterior plate is deformable by a user.

6. The interbody system of claim 1, wherein the at least a first portion of the cage body is disposed on the second portion of the cage body using a laser deposition process.

7. The interbody system of claim 1, wherein the at least a first portion of the cage body comprises a surface layer of silicon nitride.

8. The interbody system of claim 1, wherein the at least a first portion of the cage body is disposed on the second portion of the cage body using a surface coating process.

9. The interbody system of claim 1, wherein the at least a first portion of the cage body is disposed on the second portion of the cage body using a brazing process.

10. The interbody system of claim 1, wherein the at least a first portion of the cage body is disposed on the second portion of the cage body using a welding process.

11. The interbody system of claim 1, wherein the at least a first portion of the cage body is disposed on the second portion of the cage body using a bonding process.

12. The interbody system of claim 1, wherein the at least a first portion of the cage body is disposed on the second portion of the cage body using a powder deposition process.

13. The interbody system of claim 1, wherein the at least a first portion of the cage body is disposed on the second portion of the cage body using a polymer curing process.

14. The interbody system of claim 1, wherein the graft chamber comprises a silicon nitride block.

15. The interbody system of claim 1, wherein the graft chamber comprises a hollow silicon nitride block.

16. The interbody system of claim 14, wherein the graft chamber further comprises a silicon nitride block having at least one opening extending completely therethrough.

* * * * *